United States Patent [19]

McCormick et al.

[11] Patent Number: 4,966,843

[45] Date of Patent: Oct. 30, 1990

[54] EXPRESSION OF INTERFERON GENES IN CHINESE HAMSTER OVARY CELLS

[75] Inventors: Francis P. McCormick, Albany; Michael A. Innis, Oakland; Gordon M. Ringold, Palo Alto, all of Calif.

[73] Assignee: Cetus Corporation, Emeryville, Calif.

[21] Appl. No.: 761,180

[22] Filed: Jul. 31, 1985

Related U.S. Application Data

[63] Continuation-in-part of Ser. No. 438,991, Nov. 1, 1982.

[51] Int. Cl.$^5$ .................... C12P 28/00; C12N 15/00; C12N 5/00; C07H 21/04

[52] U.S. Cl. .......................... 435/69.51; 435/70.1; 435/70.3; 435/70.5; 435/172.1; 435/172.3; 435/240.2; 435/320; 435/811; 536/27; 935/11; 935/34; 935/70

[58] Field of Search .............. 435/68, 70, 71, 91, 435/172.1, 172.3, 240.1, 240.2, 811, 320, 69.51, 70.3, 70.1, 70.5; 935/11, 34, 70; 536/27

[56] References Cited

U.S. PATENT DOCUMENTS 4,399,216  8/1983  Axel et al. .................... 435/6
4,656,134  4/1987  Ringold ........................ 435/91

OTHER PUBLICATIONS

Ringold et al., J. Mol. Appl. Genet. 1:165 (1982).
Subramani et al., Mol. Cell. Biol. 1:854 (1981).
Weiss, in *RNA Tumor Viruses*, Cold Spring Harbor Laboratory, 1982, pp. 851–852.
Schimke, *Scientific American*, 243:60–69 (1980).
Ohno et al., *Nucl. Acids Res.*, 10:967–977 (1982).
Gorman et al., *Chemical Abstracts*, vol. 97:193968f (1982).
Mantei et al., *Nature*, 297:128–132 (1982).

*Primary Examiner*—James Martinell
*Attorney, Agent, or Firm*—Philip L. McGarrigle; Janet E. Hasak; Albert P. Halluin

[57] ABSTRACT

DNA constructs are prepared which operably link human interferon genes, selective, eukaryotic marker genes, and promoter and expression control sequences for the expression of human interferon in Chinese hamster ovary (CHO) cells or progeny thereof. The human recombinant interferon so produced contains glycans which are a subset of the population of glycans which are contained in the native counterpart, and may be used in therapeutic formulations. The CHO cells yield high levels of human interferon with no detectable amounts of host IFN, either constitutive or inductive.

21 Claims, 17 Drawing Sheets

```
         10         20         30         40         50         60
AGATCTGAGC ACAAAACAAG GTCTTCAGAG AAGAGCCCAA GGTTCAGGGT CACTCAATCT
TCTAGACTCG TGTTTTGTTC CAGAAGTCTC TTCTCGGGTT CCAAGTCCCA GTGAGTTAGA
         70         80         90        100        110        120
CAACAGCCCA GAAGCATCTG CAACCTCCCC AATGGCCTTG CCCTTTGTTT TACTGATGGC
GTTGTCGGGT CTTCGTAGAC GTTGGAGGGG TTACCGGAAC GGGAAACAAA ATGACTACCG
        130        140        150        160        170        180
CCTGGTGGTG CTCAACTGCA AGTCAATCTG TTCTCTGGGC TGTGATCTGC CTCAGACCCA
GGACCACCAC GAGTTGACGT TCAGTTAGAC AAGAGACCCG ACACTAGACG GAGTCTGGGT
        190        200        210        220        230        240
CAGCCTGAGT AACAGGAGGA CTTTGATGAT AATGGCACAA ATGGGAAGAA TCTCTCCTTT
GTCGGACTCA TTGTCCTCCT GAAACTACTA TTACCGTGTT TACCCTTCTT AGAGAGGAAA
        250        260        270        280        290        300
CTCCTGCCTG AAGGACAGAC ATGACTTTGG ATTTCCTCAG GAGGAGTTTG ATGGCAACCA
GAGGACGGAC TTCCTGTCTG TACTGAAACC TAAAGGAGTC CTCCTCAAAC TACCGTTGGT
        310        320        330        340        350        360
GTTCCAGAAG GCTCAAGCCA TCTCTGTCCT CCATGAGATG ATCCAGCAGA CCTTCAATCT
CAAGGTCTTC CGAGTTCGGT AGAGACAGGA GGTACTCTAC TAGGTCGTCT GGAAGTTAGA
        370        380        390        400        410        420
CTTCAGCACA AAGGACTCAT CTGCTACTTG GGATGAGACA CTTCTAGACA AATTCTACAC
GAAGTCGTGT TTCCTGAGTA GACGATGAAC CCTACTCTGT GAAGATCTGT TTAAGATGTG
        430        440        450        460        470        480
TGAACTTTAC CAGCAGCTGA ATGACCTGGA AGCCTGTATG ATGCAGGAGG TTGGAGTGGA
ACTTGAAATG GTCGTCGACT TACTGGACCT TCGGACATAC TACGTCCTCC AACCTCACCT
        490        500        510        520        530        540
AGACACTCCT CTGATGAATG TGGACTCTAT CCTGACTGTG AGAAAATACT TTCAAAGAAT
TCTGTGAGGA GACTACTTAC ACCTGAGATA GGACTGACAC TCTTTTATGA AAGTTTCTTA
        550        560        570        580        590        600
CACTCTCTAT CTGACAGAGA AGAAATACAG CCCTTGTGCA TGGGAGGTTG TCAGAGCAGA
GTGAGAGATA GACTGTCTCT TCTTTATGTC GGGAACACGT ACCCTCCAAC AGTCTCGTCT
        610        620        630        640        650        660
AATCATGAGA TCCTTCTCTT TATCAGCAAA CTTGCAAGAA AGATTAAGGA GGAAGGAATG
TTAGTACTCT AGGAAGAGAA ATAGTCGTTT GAACGTTCTT TCTAATTCCT CCTTCCTTAC
        670        680        690        700        710        720
AAAACTGGTT CAACATCGAA ATGATTCTCA TTGACTAGTA CACCATTTCA CACTTCTTGA
TTTTGACCAA GTTGTAGCTT TACTAAGAGT AACTGATCAT GTGGTAAAGT GTGAAGAACT
        730        740        750        760        770        780
GTTCTGCCGT TTCAAATATT AATTTCTGCT ATATCCATGA CTTGAGTTGA ATCAAAATTT
CAAGACGGCA AAGTTTATAA TTAAAGACGA TATAGGTACT GAACTCAACT TAGTTTTAAA
        790        800        810        820        830
TCAAACGTTT CACACGTGTT AAGCAACACT TCTTTAGCTC CACAGGGACA AAA
AGTTTGCAAA GTGTGCACAA TTCGTTGTGA AGAAATCGAG GTGTCCCTGT TTT
```

Figure 8

```
1
Met Ala Leu Pro Phe Val Leu Leu Met Ala Leu Val Val Leu Asn Cys Lys Ser Ile Cys
ATG GCC TTG CCC TTT GTT TTA CTG ATG GCC CTG GTG GTG CTC AAC TGC AAG TCA ATC TGT

21
Ser Leu Gly Cys Asp Leu Pro Gln Thr His Ser Leu Ser Asn Arg Arg Thr Leu Met Ile
TCT CTG GGC TGT GAT CTG CCT CAG ACC CAC AGC CTG AGT AAC AGG AGG ACT TTG ATG ATA

41
Met Ala Gln Met Gly Arg Ile Ser Pro Phe Ser Cys Leu Lys Asp Arg His Asp Phe Gly
ATG GCA CAA ATG GGA AGA ATC TCT CCT TTC TCC TGC CTG AAG GAC AGA CAT GAC TTT GGA

61
Phe Pro Gln Glu Glu Phe Asp Gly Asn Gln Phe Gln Lys Ala Gln Ala Ile Ser Val Leu
TTT CCT CAG GAG GAG TTT GAT GGC AAC CAG TTC CAG AAG GCT CAA GCC ATC TCT GTC CTC

81
His Glu Met Ile Gln Gln Thr Phe Asn Leu Phe Ser Thr Lys Asp Ser Ser Ala Thr Trp
CAT GAG ATG ATC CAG CAG ACC TTC AAT CTC TTC AGC ACA AAG GAC TCA TCT GCT ACT TGG

101
Asp Glu Thr Leu Leu Asp Lys Phe Tyr Thr Glu Leu Tyr Gln Gln Leu Asn Asp Leu Glu
GAT GAG ACA CTT CTA GAC AAA TTC TAC ACT GAA CTT TAC CAG CAG CTG AAT GAC CTG GAA

121
Ala Cys Met Met Gln Glu Val Gly Val Glu Asp Thr Pro Leu Met Asn Val Asp Ser Ile
GCC TGT ATG ATG CAG GAG GTT GGA GTG GAA GAC ACT CCT CTG ATG AAT GTG GAC TCT ATC

141
Leu Thr Val Arg Lys Tyr Phe Gln Arg Ile Thr Leu Tyr Leu Thr Glu Lys Lys Tyr Ser
CTG ACT GTG AGA AAA TAC TTT CAA AGA ATC ACT CTC TAT CTG ACA GAG AAG AAA TAC AGC

161
Pro Cys Ala Trp Glu Val Val Arg Ala Glu Ile Met Arg Ser Phe Ser Leu Ser Ala Asn
CCT TGT GCA TGG GAG GTT GTC AGA GCA GAA ATC ATG AGA TCC TTC TCT TTA TCA GCA AAC

181
Leu Gln Glu Arg Leu Arg Arg Lys Glu
TTG CAA GAA AGA TTA AGG AGG AAG GAA
```

Figure 10

```
  1
 GAA TTC CGA CAT CAT AAC GGT TCT GGC AAA TAT TCT GAA ATG AGC TGT TGA CAA TTA ATC
 Eco RI

61                                                                      Met Cys
 ATC GAA CTA GTT AAC TAG TAC GCA AGT TCA CGT AAA AAG GGT ATC GAT AAG CTT ATG TGT

121
 Asp Leu Pro Gln Thr His Ser Leu Ser Asn Arg Arg Thr Leu Met Ile Met Ala Gln Met
 GAT CTG CCT CAG ACC CAC AGC CTG AGT AAC AGG AGG ACT TTG ATG ATA ATG GCA CAA ATG
 Sau 3A
 181
 Gly Arg Ile Ser Pro Phe Ser Cys Leu Lys Asp Arg His Asp Phe Gly Phe Pro Gln Glu
 GGA AGA ATC TCT CCT TTC TCC TGC CTG AAG GAC AGA CAT GAC TTT GGA TTT CCT CAG GAG

241
 Glu Phe Asp Gly Asn Gln Phe Gln Lys Ala Gln Ala Ile Ser Val Leu His Glu Met Ile
 GAG TTT GAT GGC AAC CAG TTC CAG AAG GCT CAA GCC ATC TCT GTC CTC CAT GAG ATG ATC

301
 Gln Gln Thr Phe Asn Leu Phe Ser Thr Lys Asp Ser Ser Ala Thr Trp Asp Glu Thr Leu
 CAG CAG ACC TTC AAT CTC TTC AGC ACA AAG GAC TCA TCT GCT ACT TGG GAT GAG ACA CTT

361
 Leu Asp Lys Phe Tyr Thr Glu Leu Tyr Gln Gln Leu Asn Asp Leu Glu Ala Cys Met Met
 CTA GAC AAA TTC TAC ACT GAA CTT TAC CAG CAG CTG AAT GAC CTG GAA GCC TGT ATG ATG

421
 Gln Glu Val Gly Val Glu Asp Thr Pro Leu Met Asn Val Asp Ser Ile Leu Thr Val Arg
 CAG GAG GTT GGA GTG GAA GAC ACT CCT CTG ATG AAT GTG GAC TCT ATC CTG ACT GTG AGA

481
 Lys Tyr Phe Gln Arg Ile Thr Leu Tyr Leu Thr Glu Lys Lys Tyr Ser Pro Cys Ala Trp
 AAA TAC TTT CAA AGA ATC ACT CTC TAT CTG ACA GAG AAG AAA TAC AGC CCT TGT GCA TGG

541
 Glu Val Val Arg Ala Glu Ile Met Arg Ser Phe Ser Leu Ser Ala Asn Leu Gln Glu Arg
 GAG GTT GTC AGA GCA GAA ATC ATG AGA TCC TTC TCT TTA TCA GCA AAC TTG CAA GAA AGA

601
 Leu Arg Arg Lys Glu ***
 TTA AGG AGG AAG GAA TGA AAA CTG GTT CAA CAT CGA AAT GAT TCT CAT TGA CTA GTA CAC

661
 ATA AGC TT
   Hind III
```

Figure 11

```
           10         20         30         40         50         60
     GTCTTCAGAA AACCTAGAGG CCGAAGTTCA AGGTTATCCA TCTCAAGTAG CCTAGCAATA
     CAGAAGTCTT TTGGATCTCC GGCTTCAAGT TCCAATAGGT AGAGTTCATC GGATCGTTAT
           70         80         90        100        110        120
     TTTGCAACAT CCCAATGGCC CTGTCCTTTT CTTTACTGAT GGCCGTGCTG GTGCTCAGCT
     AAACGTTGTA GGGTTACCGG GACAGGAAAA GAAATGACTA CCGGCACGAC CACGAGTCGA
          130        140        150        160        170        180
     ACAAATCCAT CTGTTCTCTG GGCTGTGATC TGCCTCAGAC CCACAGCCTG GGTAATAGGA
     TGTTTAGGTA GACAAGAGAC CCGACACTAG ACGGAGTCTG GGTGTCGGAC CCATTATCCT
          190        200        210        220        230        240
     GGGCCTTGAT ACTCCTGGCA CAAATGGGAA GAATCTCTCA TTTCTCCTGC CTGAAGGACA
     CCCGGAACTA TGAGGACCGT GTTTACCCTT CTTAGAGAGT AAAGAGGACG GACTTCCTGT
          250        260        270        280        290        300
     GACATGATTT CGGATTCCCC GAGGAGGAGT TTGATGGCCA CCAGTTCCAG AAGGCTCAAG
     CTGTACTAAA GCCTAAGGGG CTCCTCCTCA AACTACCGGT GGTCAAGGTC TTCCGAGTTC
          310        320        330        340        350        360
     CCATCTCTGT CCTCCATGAG ATGATCCAGC AGACCTTCAA TCTCTTCAGC ACAGAGGACT
     GGTAGAGACA GGAGGTACTC TACTAGGTCG TCTGGAAGTT AGAGAAGTCG TGTCTCCTGA
          370        380        390        400        410        420
     CATCTGCTGC TTGGGAACAG AGCCTCCTAG AAAAATTTTC CACTGAACTT TACCAGCAAC
     GTAGACGACG AACCCTTGTC TCGGAGGATC TTTTTAAAAG GTGACTTGAA ATGGTCGTTG
          430        440        450        460        470        480
     TGAATGACCT GGAAGCATGT GTGATACAGG AGGTTGGGGT GGAAGAGACT CCCCTGATGA
     ACTTACTGGA CCTTCGTACA CACTATGTCC TCCAACCCCA CCTTCTCTGA GGGGACTACT
          490        500        510        520        530        540
     ATGAGGACTC CATCCTGGCT GTGAGGAAAT ACTTCCAAAG AATCACTCTT TATCTAACAG
     TACTCCTGAG GTAGGACCGA CACTCCTTTA TGAAGGTTTC TTAGTGAGAA ATAGATTGTC
          550        560        570        580        590        600
     AGAAGAAATA CAGCCCTTGT GCCTGGGAGG TTGTCAGAGC AGAAATCATG AGATCCCTCT
     TCTTCTTTAT GTCGGGAACA CGGACCCTCC AACAGTCTCG TCTTTAGTAC TCTAGGGAGA
          610        620        630        640        650        660
     CGTTTTCAAC AAACTTGCAA AAAAGATTAA GGAGGAAGGA TTGAAACCTG GTTCAACATG
     GCAAAGTTG TTTGAACGTT TTTTCTAATT CCTCCTTCCT AACTTTGGAC CAAGTTGTAC
          670        680        690        700        710        720
     GAAATGATCC TGATTGACTA ATACATTATC TCACACTTTC ATGAGTTCTT CCATTTCAAA
     CTTTACTAGG ACTAACTGAT TATGTAATAG AGTGTGAAAG TACTCAAGAA GGTAAAGTTT
          730        740        750        760        770        780
     GACTCACTTC TATAACCACC ACGAGTTGAA TCAAAATTTT CAAATGTTTT CAGCAGTGTG
     CTGAGTGAAG ATATTGGTGG TGCTCAACTT AGTTTTAAAA GTTTACAAAA GTCGTCACAC
          790        800        810        820        830        840
     AAGAAGCTTG GTGTATACCT GTGCAGGCAC TAGTCCTTTA CAGATGACAA TGCTGATGTC
     TTCTTCGAAC CACATATGGA CACGTCCGTG ATCAGGAAAT GTCTACTGTT ACGACTACAG
          850        860        870
     TCTGTTCATC TATTTATTTA AATATTTATT TATTTT
     AGACAAGTAG ATAAATAAAT TTATAAATAA ATAAAA
```

Figure 14

```
  1
Met Ala Leu Ser Phe Ser Leu Leu Met Ala Val Leu Val Leu Ser Tyr Lys Ser Ile Cys
ATG GCC CTG TCC TTT TCT TTA CTG ATG GCC GTG CTG GTG CTC AGC TAC AAA TCC ATC TGT

21
Ser Leu Gly Cys Asp Leu Pro Gln Thr His Ser Leu Gly Asn Arg Arg Ala Leu Ile Leu
TCT CTG GGC TGT GAT CTG CCT CAG ACC CAC AGC CTG GGT AAT AGG AGG GCC TTG ATA CTC

41
Leu Ala Gln Met Gly Arg Ile Ser His Phe Ser Cys Leu Lys Asp Arg His Asp Phe Gly
CTG GCA CAA ATG GGA AGA ATC TCT CAT TTC TCC TGC CTG AAG GAC AGA CAT GAT TTC GGA

61
Phe Pro Glu Glu Glu Phe Asp Gly His Gln Phe Gln Lys Ala Gln Ala Ile Ser Val Leu
TTC CCC GAG GAG GAG TTT GAT GGC CAC CAG TTC CAG AAG GCT CAA GCC ATC TCT GTC CTC

81
His Glu Met Ile Gln Gln Thr Phe Asn Leu Phe Ser Thr Glu Asp Ser Ser Ala Ala Trp
CAT GAG ATG ATC CAG CAG ACC TTC AAT CTC TTC AGC ACA GAG GAC TCA TCT GCT GCT TGG

101
Glu Gln Ser Leu Leu Glu Lys Phe Ser Thr Glu Leu Tyr Gln Gln Leu Asn Asp Leu Glu
GAA CAG AGC CTC CTA GAA AAA TTT TCC ACT GAA CTT TAC CAG CAA CTG AAT GAC CTG GAA

121
Ala Cys Val Ile Gln Glu Val Gly Val Glu Glu Thr Pro Leu Met Asn Glu Asp Ser Ile
GCA TGT GTG ATA CAG GAG GTT GGG GTG GAA GAG ACT CCC CTG ATG AAT GAG GAC TCC ATC

141
Leu Ala Val Arg Lys Tyr Phe Gln Arg Ile Thr Leu Tyr Leu Thr Glu Lys Lys Tyr Ser
CTG GCT GTG AGG AAA TAC TTC CAA AGA ATC ACT CTT TAT CTA ACA GAG AAG AAA TAC AGC

161
Pro Cys Ala Trp Glu Val Val Arg Ala Glu Ile Met Arg Ser Leu Ser Phe Ser Thr Asn
CCT TGT GCC TGG GAG GTT GTC AGA GCA GAA ATC ATG AGA TCC CTC TCG TTT TCA ACA AAC

181
Leu Gln Lys Arg Leu Arg Arg Lys Asp
TTG CAA AAA AGA TTA AGG AGG AAG GAT
```

Figure 16

```
  1
GAA TTC CGA CAT CAT AAC GGT TCT GGC AAA TAT TCT GAA ATG AGC TGT TGA CAA TTA ATC
 Eco RI

61                                                                      Met Cys
ATC GAA CTA GTT AAC TAG TAC GCA AGT TCA CGT AAA AAG GGT ATC GAT AAG CTT ATG TGT

121
Asp Leu Pro Gln Thr His Ser Leu Gly Asn Arg Arg Ala Leu Ile Leu Leu Ala Gln Met
GAT CTG CCT CAG ACC CAC AGC CTG GGT AAT AGG AGG GCC TTG ATA CTC CTG GCA CAA ATG
Sau 3A
181
Gly Arg Ile Ser His Phe Ser Cys Leu Lys Asp Arg His Asp Phe Gly Phe Pro Glu Glu
GGA AGA ATC TCT CAT TTC TCC TGC CTG AAG GAC AGA CAT GAT TTC GGA TTC CCC GAG GAG
                                                                      Ava I
241
Glu Phe Asp Gly His Gln Phe Gln Lys Ala Gln Ala Ile Ser Val Leu His Glu Met Ile
GAG TTT GAT GGC CAC CAG TTC CAG AAG GCT CAA GCC ATC TCT GTC CTC CAT GAG ATG ATC

301
Gln Gln Thr Phe Asn Leu Phe Ser Thr Glu Asp Ser Ser Ala Ala Trp Glu Gln Ser Leu
CAG CAG ACC TTC AAT CTC TTC AGC ACA GAG GAC TCA TCT GCT GCT TGG GAA CAG AGC CTC

361
Leu Glu Lys Phe Ser Thr Glu Leu Tyr Gln Gln Leu Asn Asp Leu Glu Ala Cys Val Ile
CTA GAA AAA TTT TCC ACT GAA CTT TAC CAG CAA CTG AAT GAC CTG GAA GCA TGT GTG ATA

421
Gln Glu Val Gly Val Glu Glu Thr Pro Leu Met Asn Glu Asp Ser Ile Leu Ala Val Arg
CAG GAG GTT GGG GTG GAA GAG ACT CCC CTG ATG AAT GAG GAC TCC ATC CTG GCT GTG AGG

481
Lys Tyr Phe Gln Arg Ile Thr Leu Tyr Leu Thr Glu Lys Lys Tyr Ser Pro Cys Ala Trp
AAA TAC TTC CAA AGA ATC ACT CTT TAT CTA ACA GAG AAG AAA TAC AGC CCT TGT GCC TGG

541
Glu Val Val Arg Ala Glu Ile Met Arg Ser Leu Ser Phe Ser Thr Asn Leu Gln Lys Arg
GAG GTT GTC AGA GCA GAA ATC ATG AGA TCC CTC TCG TTT TCA ACA AAC TTG CAA AAA AGA

601
Leu Arg Arg Lys Asp ***
TTA AGG AGG AAG GAT TGA AAC CTG GTT CAA CAT GGA AAT GAT CCT GAT TGA CTA ATA CAT

661
TAT CTC ACA CTT TCA TGA GTT CTT CCA TTT CAA AGA CTC ACT TCT ATA ACC ACC ACG AGT

721
TGA ATC AAA ATT TTC AAA TGT TTT CAG CAG TGT GAA GAA GCT T
                                                 Hind III
```

Figure 17

EXPRESSION OF INTERFERON GENES IN CHINESE HAMSTER OVARY CELLS

BACKGROUND OF THE INVENTION

This application is a continuation-in-part application of copending U.S. Application Ser. No. 438,991, filed Nov. 1, 1982, now abandoned. This application is also related to copending U.S. Application Ser. No. 338,704, filed Jan. 11, 1982.

This application relates to human interferons and their production in Chinese hamster ovary cells and therapeutic formulations including the human interferons so produced.

Interferons (IFNs) are relatively small, species-specific, single chain polypeptides, produced by mammalian cells in response to exposure to a variety of inducers such as viruses, polypeptides, mitogens and the like. They exhibit antiviral, antiproliferative and immunoregulatory properties and are, therefore, of great interest as therapeutic agents in the control of cancer and various other antiviral diseases (J. Desmyter et al., Lancet 11, 645-647 (1976); R. Derynck et al., Nature 287, 193 (1980)). Human IFNs are classified into three major types, fibroepithelial (IFN-$\beta$), leukocyte (IFN-$\alpha$) and immune (IFN-$\gamma$).

Although IFNs have been known for nearly twenty-five years, characterization of the molecules in terms of their structure and properties has been hampered by the paucity of material available for such studies. Naturally occurring or native IFNs have to be isolated and purified from human sources, which is a very time-consuming and expensive process. Clinical studies to demonstrate the use of IFNs as therapeutic agents have, likewise, been severely limited by the small amounts of pure material available.

In recent times, with the advent of recombinant DNA technology, IFN genes have been identified, isolated, cloned and expressed in microorganisms. Several IFN-$\alpha$ genes have been cloned and expressed in *E. coli* (Nagata, S., et al., Nature 284:316-320 (1980); Goeddel, D. V., et al., Nature 287:411-415 (1980); Yelverton, E., et al., Nucleic Acids Research, 9:731-741, (1981); Streuli, M., et al., Proc. Natl. Acad. Sci., (USA), 78:2848-2852 (1981).

Similarly, IFN-$\beta$ gene has been cloned and expressed in *E. coli* (Taniguchi, et al., Gene 10, 11-15 (1980)).

Although at least some IFNs are believed to be glycoproteins, IFN-$\beta$ has been shown to be a glycoprotein by chemical measurement of its carbohydrate content. It has one N-glycosidyl attachment site (E. Knight, Jr., Proc. Natl. Acad. Sci., 73, 520 (1976); E. Knight, Jr., and D. Fahey, J. Interferon Res., 2 (3), 421 (1982)). Even though not much is known about the kinds of sugars which make up the carbohydrate moiety of IFN-$\beta$, it has been shown that the carbohydrate moiety is not essential for its antigenicity, biological activity or hydrophobicity (T. Taniguchi et al., supra; E. Knight, Jr., supra; and E. Knight, Jr. and D. Fahey, supra). *E. coli*, which is commonly used as a host for the expression of the IFN-$\beta$ gene, has no mechanism for attachment of carbohydrates to proteins. The IFN-$\beta$ produced in *E. coli* by recombinant DNA technology has in vitro antiviral activity similar to that of native IFN-$\beta$, indicating that glycosylation is probably not essential for full biological activity. However, studies of *E. coli*-produced IFN-$\beta$ suggest that although it retains biological activity similar to that of native human IFN-$\beta$ even without the glycosyl moieties, it exhibits altered physical properties which may be due in part to the absence of glycosyl residues. For correct characterization of IFNs and for studying of their efficacy as therapeutic agents, it would be desirable to produce them in animal hosts where the protein would be expected to be glycosylated and in the conformation closest to that of native human IFNs. There have been, however, technical problems involved with introducing DNA fragments into animal tissue culture cells which are quite impermeable to nucleic acids. Other problems relating to the production of the host IFN which may be antigenic to other species have had to be addressed and solved, as these samples would not be suitable for clinical and therapeutic uses.

International Patent Application No. PCT/US81/00240, published Sept. 3, 1981, broadly describes processes for inserting DNA into eukaryotic cells and for producing proteinaceous material, but provides no enabling details regarding suitable DNA fragments, hosts, transforming vectors, methods for transformation, promoter and control sequences which facilitate expression, and other essential components.

It would be highly desirable, therefore, to be able to produce human IFNs in mammalian cells, either constitutively or by induction, without the parallel production of the endogenous host IFN.

SUMMARY OF THE INVENTION

Accordingly, the present invention provides a DNA construct for the expression of the human interferon gene in Chinese hamster ovary cells or progeny thereof comprising an operable linkage of:
  (a) a nucleotide sequence from a cloning vector which allows for replication in a prokaryotic cell;
  (b) a first gene capable of transcription and translation in Chinese hamster ovary cells or progeny thereof operably linked to a selectable marker for the selection of Chinese hamster ovary (CHO) cell transformants or progeny thereof; and
  (c) a human interferon gene capable of transcription and translation in Chinese hamster ovary cells or progeny thereof.

In other aspects, the invention provides for transforming vectors carrying the DNA construct, suitable CHO hosts transformed with the cloning vector, and expression control sequences for expressing the DNA fragments.

The present invention also provides a method for producing human interferon in CHO cells or progeny thereof comprising:
  (a) introducing into a Chinese hamster ovary cell or progeny thereof the above-described DNA construct;
  (b) selecting transformed cells;
  (c) growing the selected transformants under selective conditions whereby the interferon gene in said DNA construct is expressed; and
  (d) selecting mutants of the grown transformants which are resistant to the negative growth effects of human interferon.

In yet another aspect, the invention provides human interferon produced by the above method, methods of providing interferon therapy to humans using the interferon, and therapeutic formulations comprising an effective amount of the interferon in a carrier medium.

In preferred embodiments, DNA fragments which code for one or more IFNs are isolated from appropriate human cells; introduced into CHO cells by DNA transfection, or by penetration of viral vectors carrying the DNA fragment, or by transfection of cloned plasmids into cells that express T-antigens; and expressed by the host cells; and the expressed product is isolated and purified.

BRIEF DESCRIPTION OF THE DRAWINGS

FIG. 8 is the nucleotide sequence of the structural gene coding for IFN-$\alpha$61.

FIG. 10 depicts the amino acid sequence of the 23 amino acid signal polypeptide and the 166 amino acid mature IFN-$\alpha$61 coded for by the gene depicted in FIG. 8.

FIG. 11 is the DNA sequence of the *E. coli* trp promoter and the gene of FIG. 8 which was inserted between the EcoRI and HindIII sites of the plasmid pBW11.

FIG. 14 is the nucleotide sequence of the structural gene coding for IFN-$\alpha$76.

FIG. 16 shows the amino acid sequence of the 23 amino acid signal polypeptide and the 166 amino acid mature IFN-$\alpha$76 coded for by the gene depicted in FIG. 14.

FIG. 17 is the DNA sequence of the *E. coli* trp promoter and the gene of FIG. 14 which was inserted between the Eco RI and HindIII sites of the plasmid pBR322.

DESCRIPTION OF THE PREFERRED EMBODIMENTS

Figure 1:
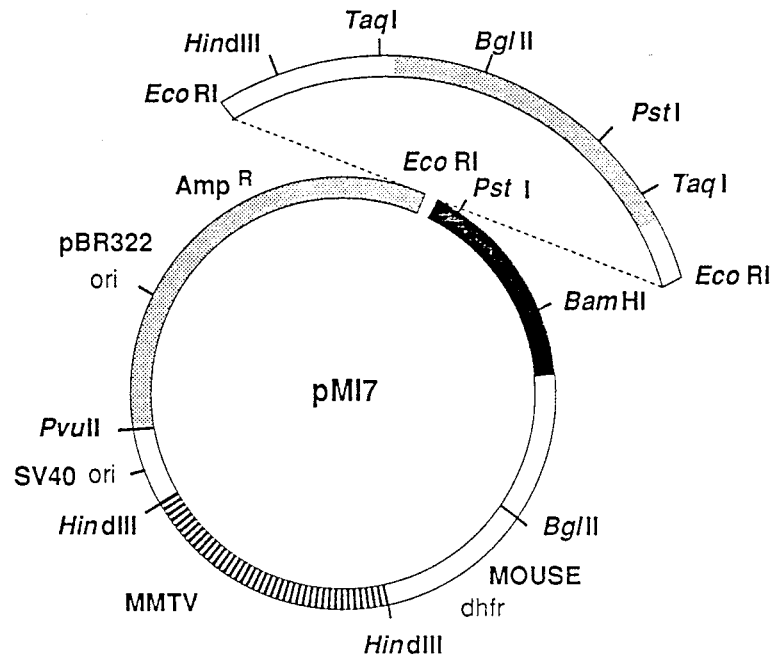
FIG. 1 is a diagram of plasmid pM17 carrying the human IFN-$\beta$ gene.

The term "lipophilic protein" as used herein refers to those proteins which are insoluble or not readily soluble in water or an aqueous medium under ambient conditions of room temperature and atmospheric pressure at a pH of between about 6 and 8, i.e., at about neutral or physiological pH. Examples of such proteins include interleukin-2 (IL-2) and interferon-$\beta$ (IFN-$\beta$).

The term "interferon-$\beta$" as used herein refers to interferon-$\beta$ produced by recombinant DNA technology as described in the art having sequence homology with, and the functionality, including bioactivity, of native interferon-$\beta$.

The precise chemical structure of the lipophilic protein will depend on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through posttranslational processing systems of the producing host; other such modifications may be introduced in vitro. In any event, such modifications are included in the definition of protein herein so long as the activity of the protein, as defined above, is not destroyed. It is expected, of course, that such modifications may quantitatively or qualitatively affect the activity, by either enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Finally, modification to the primary structure itself by deletion, addition, or alteration of the amino acids incorporated into the sequence during translation can be made without destroying the activity of the protein. For example, at least one cysteine residue which is not essential to biological activity, is present in the biologically active protein, and is free to form a disulfide link may be deleted or replaced with another amino acid to eliminate sites for intermolecular crosslinking or incorrect intramolecular disulfide bond formation. Such modified proteins, known as "muteins," are described in U.S. Pat. No. 4,518,584, issued May 21, 1985. In another example, a neutral amino acid of a biologically active protein such as IL-2 or IFN-$\beta$ is substituted for each methionine residue susceptible to chloramine T or peroxide oxidation, wherein additional, non-susceptible methionine residues are not so substituted. A neutral amino acid alteration in this context is defined as one which does not adversely affect biological activity and involves uncharged or non-polar amino acid substitutions or deletion of the methionine. In preferred examples of this embodiment the methionine at amino acid position 104 of IL-2 is replaced by an alanine residue or the cysteine at amino acid position 17 of IFN-$\beta$ is replaced by a serine residue.

The term "operably linked" or "operable linkage" as used herein regarding DNA sequences or genes refers to the situation wherein the sequences or genes are juxtaposed in such a manner so as to permit their ordinary functionality. For example, a promoter operably linked to a coding sequence refers to those linkages where the promoter is capable of controlling the expression of the sequence. The sequence operably linked to a selectable marker has the same significance: i.e., it permits the selectable marker to be positioned in the transcript so as to participate in the selection procedure after the sequence has been expressed in the host. Similarly, an operable linkage of sequences and genes signifies that the sequences and genes are so positioned in a DNA construct as to permit expression of the sequences in the desired manner.

The term "cells" refers to living cells whether separated from or suspended in the medium. The term "culture" in referring to cells signifies living cells suspended in the medium.

The term "progeny" as used herein regarding Chinese hamster ovary cells is intended to include all derivatives, issue, and offspring of the parent cells which, when transformed by the process of this invention, will produce the human interferon to the exclusion of its own native hamster interferon, regardless of generation.

The term "DNA construct" as used herein refers to any suitable cloning vector, including, for example, plasmids, viruses such as SV40, polyoma virus, bovine papilloma virus, mouse mammary virus and the like, and bacteriophages. Such vectors must be capable of being cloned and expressed in Chinese hamster ovary cells or progeny thereof. Plasmids and viral vectors are preferred, with derivatives of pBR322 containing various viral elements which facilitate selection in CHO cells being most preferred.

The term "capable of transcription and translation in Chinese hamster ovary cells or progeny thereof" as used herein refers to a gene which is operably linked to a promoter and to codons which initiate and terminate translation of the gene.

The term "promoter" as used herein refers to a sequence which, when operably linked to a coding sequence, enhances the expression of that sequence. A "heterologous" promoter refers to a promoter which is not native to the sequence.

Chinese hamster ovary cells or progeny thereof are used as the host cells herein. They do not coproduce endogenous (hamster) IFN constitutively or by induction, whether a promoter endogenous to IFN or a heterologous promoter for IFN is employed, in contrast to other eukaryotic hosts such as mouse cells. Furthermore, CHO cells are largely resistant to the anti-cellular activity of the human IFNs produced. When CHO cells are transformed with IFN gene under its own promoter control, expression levels for IFN are high for induction and low for constitutive production. With heterologous promoters, no detectable induction is observed, but only constitutive production of IFN.

The method of effecting expression of heterologous genes in CHO host cells or progeny thereof generally involves preparing DNA constructs as defined above operably linked to a nucleotide sequence for replicating in a prokaryotic cell, preferably E. coli ; a marker gene operably linked to a CHO cell selectable marker for the selection of transformants or progeny thereof, and operably linked to a promoter and start and stop codons; and an interferon gene from a human source, operably linked to an endogenous or heterologous promoter and translation sequences (start and stop codons) for expression of the interferon gene in CHO cells or progeny thereof. This DNA construct is then introduced in CHO cells or progeny thereof, preferably in a culture, by any technique, including any of the three techniques described below, the transformed cells are selected and then grown under selective conditions whereby the interferon gene is expressed; and the interferon so produced is isolated and purified.

Any suitable cloning vector, such as plasmids, bacteriophage, viruses including SV40, polyoma virus, bovine papilloma virus, mouse mammary tumor virus and the like can be used as the source of the nucleotide sequence for replicating in a prokaryotic cell. Plasmids and viral vectors are preferred. The plasmids used as the source in a preferred embodiment are derivatives of pBR322 containing various viral elements which facilitate selection in CHO cells.

The choice of the selectable marker operably linked to the marker gene is not critical to the practice of the subject invention and any convenient auxotrophic or other marker such as dihydrofolate reductase, antibiotic resistance, toxin and heavy metal resistance or viral immunity can be employed. Dihydrofolate reductase and antibiotic resistance are preferred, with dihydrofolate reductase being most preferred. The gene is also operably linked to a promoter, preferably its own endogeneous promoter, and start and stop codons by any suitable technique known in the art.

Interferon genes are obtained from a human source. In preferred embodiments, human IFN-α and IFN-β genes are used for expression, obtained from human leukocytes or fibroblastoid cells, respectively. More specifically, genes encoding human IFN-αs, designated as IFN-α61 and IFN-α76, and IFN-$\beta_1$ were chosen for expression. IFN-β, and most preferably IFN-$\beta_1$, are preferred genes herein. The DNA coding sequences and methods for the screening and selection of the DNA sequences, promoter and translation sequences for the expression of IFN-α61 and IFN-α76 are described in commonly owned, copending U.S. patent applications, Ser. Nos. 414,054 and 414,053 filed Sept. 3, 1982, respectively.

IFN-α61

The IFN-α61 is a polypeptide having interferon activity and comprising the amino acid sequence:

| | | | |
|---|---|---|---|
| CysAspLeuProGln | ThrHisSerLeuSer | AsnArgArgThrLeu | MetIleMetAlaGln |
| MetGlyArgIleSer | ProPheSerCysLeu | LysAspArgHisAsp | PheGlyPheProGln |
| GluGluPheAspGly | AsnGlnPheGlnLys | AlaGlnAlaIleSer | ValLeuHisGluMet |
| IleGlnGlnThrPhe | AsnLeuPheSerThr | LysAspSerSerAla | ThrTrpAspGluThr |
| LeuLeuAspLysPhe | TyrThrGluLeuTyr | GlnGlnLeuAsnAsp | LeuGluAlaCysMet |
| MetGlnGluValGly | ValGluAspThrPro | LeuMetAsnValAsp | SerIleLeuThrVal |
| ArgLysTyrPheGln | ArgIleThrLeuTyr | LeuThrGluLysLys | TyrSerProCysAla |
| TrpGluValValArg | AlaGluIleMetArg | SerPheSerLeuSer | AlaAsnLeuGlnGlu |
| ArgLeuArgArgLys | Glu | | |

The DNA unit or fragment has the following nucleotide sequence that encodes the above-described polypeptide:

| | | | | | | | | | | | |
|---|---|---|---|---|---|---|---|---|---|---|---|
| TGT | GAT | CTG | CCT | CAG | ACC | CAC | AGC | CTG | AGT | AAC | AGG | AGG |
| ACT | TTG | ATG | ATA | ATG | GCA | CAA | ATG | GGA | AGA | ATC | TCT | CCT |
| TTC | TCC | TGC | CTG | AAG | GAC | AGA | CAT | GAC | TTT | GGA | TTT | CCT |
| CAG | GAG | GAG | TTT | GAT | GGC | AAC | CAG | TTC | CAG | AAG | GCT | CAA |
| GCC | ATC | TCT | GTC | CTC | CAT | GAG | ATG | ATC | CAG | CAG | ACC | TTC |
| AAT | CTC | TTC | AGC | ACA | AAG | GAC | TCA | TCT | GCT | ACT | TGG | GAT |
| GAG | ACA | CTT | CTA | GAC | AAA | TTC | TAC | ACT | GAA | CTT | TAC | CAG |
| CAG | CTG | AAT | GAC | CTG | GAA | GCC | TGT | ATG | ATG | CAG | GAG | GTT |
| GGA | GTG | GAA | GAC | ACT | CCT | CTG | ATG | AAT | GTG | GAC | TCT | ATC |
| CTG | ACT | GTG | AGA | AAA | TAC | TTT | CAA | AGA | ATC | ACT | CTC | TAT |
| CTG | ACA | GAG | AAG | AAA | TAC | AGC | CCT | TGT | GCA | TGG | GAG | GTT |
| GTC | AGA | GCA | GAA | ATC | ATG | AGA | TCC | TTC | TCT | TTA | TCA | GCA |
| AAC | TTG | CAA | GAA | AGA | TTA | AGG | AGG | AAG | GAA | | | |

Figure 6:
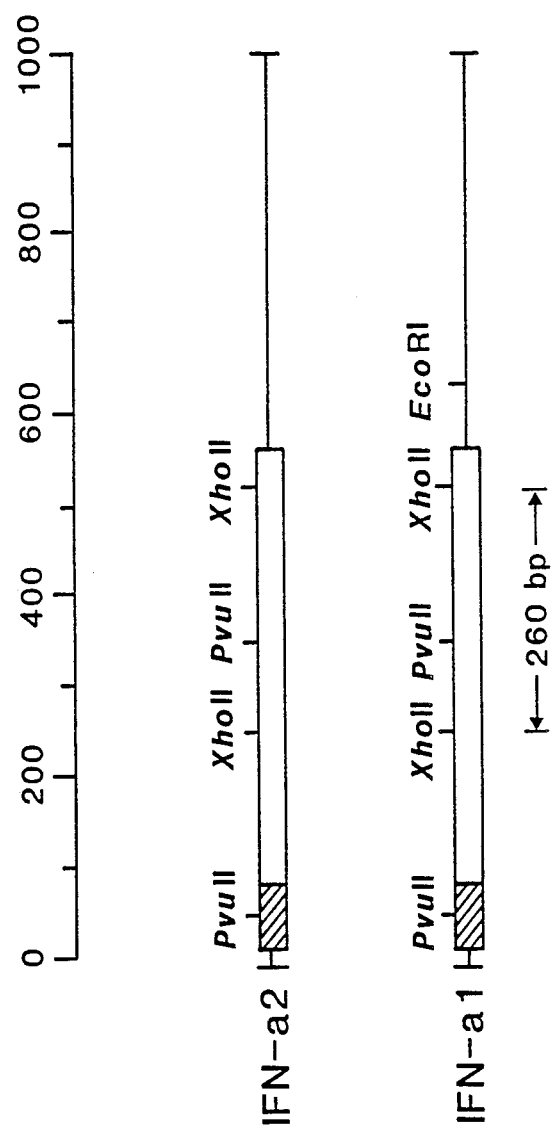
FIG. 6 is a partial restriction map showing the two Xho II restriction sites producing a 260 bp DNA fragment from the IFN-$\alpha$1 and IFN-$\alpha$2 structural genes.

FIG. 6 is a partial restriction map which shows the two XhoII restriction sites that produce a homologous 260 base pair DNA fragment from the IFN-α1 and IFN-α2 structural genes. Data for this map are from Streuli, M., et al., *Science*, 209:1343–1347 (1980).

Figure 7:
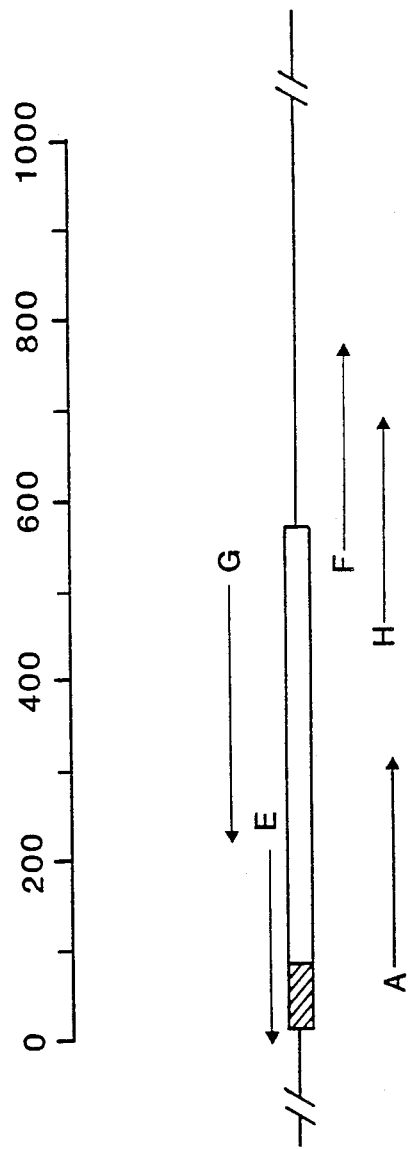
FIG. 7 is the sequence strategy used to obtain the complete DNA sequence of the IFN-$\alpha$61 gene coding region.

FIG. 7 depicts the sequencing strategy used to obtain the complete DNA sequence of the IFN-α61 gene coding region. Bacteriophage mp7:α61-1 DNA served as the template for sequences obtained with primers A, H and F and bacteriophage mp7:α61-2 DNA was the template for sequences obtained with primers E and G. The crosshatched area of the gene depicts the region that encodes the 23 amino acid signal polypeptide and the open box depicts the region that encodes the mature polypeptide. The scale, in base pairs, is numbered with 0, representing the ATG start codon of preinterferon. The arrows indicate the direction and extent of sequencing with each primer.

FIG. 8 is the nucleotide sequence of the structural gene coding for IFN-α61 including some of the flanking 5'- and 3'-noncoding regions of the gene. The region coding for preinterferon and the mature polypeptide begins with the ATG codon at position 92 and terminates with the TGA codon at position 659.

Figure 9:
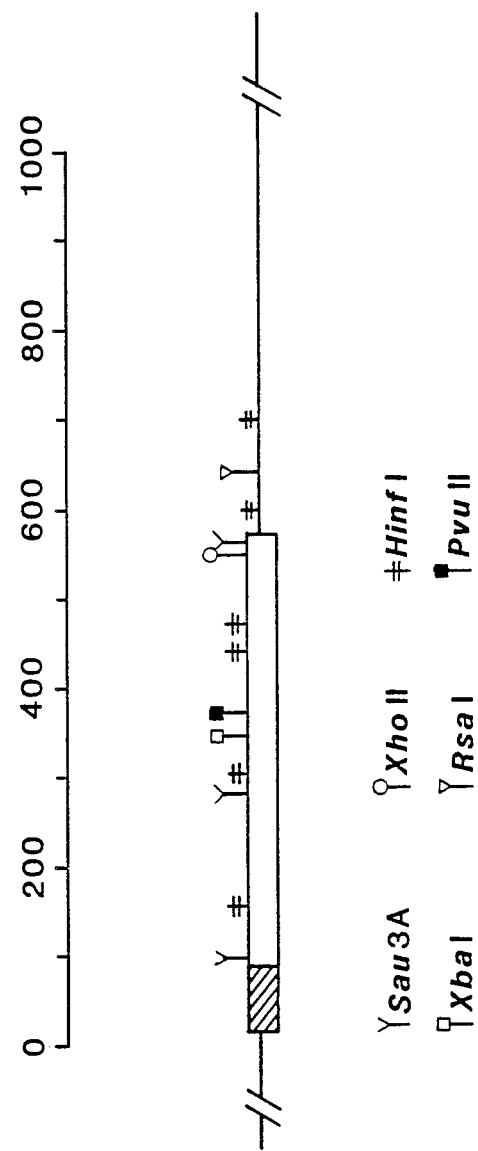
FIG. 9 is a partial restriction map of the coding region of the IFN-$\alpha$61 gene.

FIG. 9 is a partial restriction map of the coding region of the IFN-α61 gene. The crosshatching represents the region that encodes the 23 amino acid signal peptide, and the open box represents the gene coding sequence for the mature polypeptide. The scale, in base pairs, is numbered with 0, representing the ATG start codon of preinterferon.

FIG. 10 shows the amino acid sequence of the 23 amino acid signal polypeptide and the 166 amino acid mature IFN-α61 coded for by the gene depicted in FIG. 8. The 189 amino acid sequence is displayed above the corresponding nucleotide sequence. Amino acid 24, cysteine, is the first amino acid of the mature IFN-α61 protein.

FIG. 11 is the DNA sequence of the *E. coli* trp promoter and the gene of FIG. 8 which was inserted between the EcoRI and HindIII sites of the plasmid pBW11. The amino acid sequence of FIG. 11 is written above the corresponding DNA sequence and the location of the restriction sites used in the construction of the expression plasmid is indicated.

Figure 12:
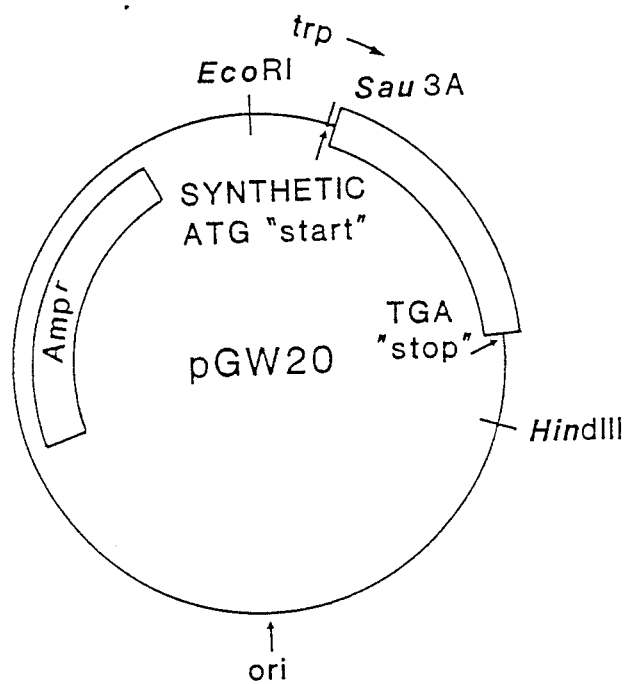
FIG. 12 is a diagram of the expression plasmid, pGW20, used to produce IFN-$\alpha$61.

FIG. 12 is a diagram of the expression plasmid, pGW20.

In general terms, IFN-α61 was made by identifying and isolating the IFN-α61 gene by screening a library of human genomic DNA with an appropriate IFN-α DNA probe, constructing a vector containing the IFN-α61 gene, transforming microorganisms with the vector, cultivating transformants that express IFN-α61, and collecting IFN-α61 from the culture. An embodiment of this procedure is described below.

DNA Probe Preparation

Total cytoplasmic RNA was extracted from human lymphoblastoid cells, Namalwa, which had been induced for IFN production by pretreatment with 5-bromodeoxyuridine (Tovey, M. G., et al., *Nature*, 267:455–457 (1977)) and Newcastle Disease Virus (NDV). The poly (A) (polyadenylic acid)-containing messenger RNA (mRNA) was isolated from total RNA by chromatography on oligo(dT)-cellulose (type 3 from Collaborative Research; Aviv, H., and Leder, P., *Proc Natl Acad Sci (USA)*, 69:1408–1412 (1972)) and enriched for IFN mRNA by density gradient centrifugation on 5%–20% sucrose gradients. Fractions containing IFN mRNA were identified by translating the aRNA by microinjecting aliquots of each fraction into Xenopus oocytes and determining the IFN activity of the products of the translations according to a method described by Colman, A., and Morser, J., *Cell*, 17:517–526 (1979).

The Namalwa cell human IFN enriched mRNA was used to construct complementary DNA (cDNA) clones in *E. coli* by the G/C tailing method using the PstI site of the cloning vector pBR322 (Bolivar, F., et al., *Gene*, 2:95–113 (1977)). A population of transformants containing approximately 50,000 individual cDNA clones was grown in one liter of medium overnight and the total plasmid DNA was isolated.

The sequences of two IFN-α clones (IFN-α1 and IFN-α2), as examples, have been published by Streuli, M., et al., *Science*, 209:1343–1347 (1980). Examination of the DNA sequences of these two clones revealed that the restriction enzyme XhoII would excise a 260 bp fragment from either the IFN-α1 or the IFN-α2 gene (see FIG. 6). XhoII was prepared in accordance with the process described by Gingeras, T. R., and Roberts, R. J., *J Mol Biol*, 118:113–122 (1978).

One mg of the purified total plasmid DNA preparation was digested with XhoII and the DNA fragments were separated on a preparative 6% polyacrylamide gel. DNA from the region of the gel corresponding to 260 bp was recovered by electroelution and recloned by ligation into the BamHI site of the single strand bacteriophage M13:mp7. Thirty-six clones were picked at random, the single-stranded DNA was isolated therefrom, and the DNA was sequenced. The DNA sequences of four of these clones were homologous to known IFN-α DNA sequences. Clone mp7:α-260, with a DNA sequence identical to IFN-α1 DNA (Streuli, M., et al., *Science*, 209:1343–1347 (1980)) was chosen as a highly specific hybridization probe for identifying additional IFN-α DNA sequences. This clone is hereinafter referred to as the "260 probe."

Screening of Genomic DNA Library for IFN-α61 Gene

In order to isolate other IFN-α gene sequences, a $^{32}$p-labeled 260 probe was used to screen a library of human genomic DNA by in situ hybridization. The human gene bank, prepared by Lawn, R. M., et al., *Cell*, 15:1157-1174 (1978), was generated by partial cleavage of fetal human DNA with HaeIII and AluI and cloned into bacteriophage λ Charon 4A with synthetic EcoRI linkers. Approximately 800,000 clones were screened, of which about 160 hybridized with the 260 probe. Each of the 160 clones was further characterized by restriction enzyme mapping and comparison with the published restriction maps of 10 chromosomal IFN genes (Nagata, S., et al., *J Interferon Research*, 1:333-336 (1981)). One of the clones, hybrid phage λ4A:α61 containing a 180 kb insert, was characterized as follows. A DNA preparation of λ4A:α61 was cleaved with HindIII, BglII, and EcoRI respectively, and the fragments were separated on an agarose gel, transferred to a nitrocellulose filter (Southern, E. M., *J Mol Biol*, 98:503-517 (1977)) and hybridized with $^{32}$P-labeled 260 probe. This procedure localized the IFN-α61 gene to a 1.9 kb BglII restriction fragment which was then isolated and re-cloned, in both orientations, by ligation of the fragment into BamHI-cleaved M13:mp7. The two subclones are designated mp7:α61-1 and mp7:α61-2. The −1 designated indicates that the single-stranded bacteriophage contains insert DNA complementary to the aRNA (the minus strand), and the −2 designation indicates that the insert DNA is the same sequence as the mRNA (the plus strand).

Sequencing of the IFN-α61 Gene

The Sanger dideoxy-technique was used to determine the DNA sequence of the IFN-α61 gene. The strategy employed is diagrammed in FIG. 7, the DNA sequence thus obtained is given in FIG. 8, and a partial restriction enzyme map of the IFN-α61 gene is illustrated in FIG. 9. Unlike many genes from eukaryotic organisms, but analogous to other IFN chromosomal genes which have been characterized, the DNA sequence of this gene demonstrates that it lacks introns. Homology to protein sequence information from these known IFN-α genes made it possible to determine the correct translational reading frame and thus allowed the entire 166 amino acid sequence of IFN-α61 to be predicted from the DNA sequence as well as a precursor segment, or signal polypeptide, of 23 amino acids (FIG. 10).

The DNA sequence of the IFN-α61 gene and the amino acid sequence predicted therefrom differ substantially from the other known IFN-α DNA and IFN-α amino acid sequences. In this regard, Goeddel, D. V., et al., *Nature*, 290:20-26 (1981) discloses the DNA sequence of a partial IFN cDNA clone, designated LeIF-G. The sequence of the partial clone is similar to the 3'-end of the IFN-α61 DNA sequence, except for a nucleotide change in the codon for amino acid 128. As compared to the partial clone, the IFN-α61 gene contains additional DNA that codes for the first 33 amino acids of IFN-α61.

Plasmid Preparation and Host Transformation (IFN-α61)

Assembly of the plasmid for direct expression of the IFN-α61 gene involved replacing the DNA fragment encoding the 23 amino acid signal polypeptide of preinterferon with a 120 bp EcoRI/Sau3A promoter fragment (*E. coli* trp promoter, operator, and trp leader ribosome binding site preceding an ATG initiation codon) and using HindIII site that was inserted, 59 nucleotides 3'- of the TGA translational stop codon, to insert the gene into the plasmid pBW11 (a derivative of pBR322 having a deletion between the HindIII and PvuII sites). The complete DNA sequence of the promoter and gene fragments inserted between the EcoRI and HindIII sites of pBW11 is shown in FIG. 11, which also shows the exact location of relevant cloning sites. Details of the construction are described below.

The coding region for mature IFN-α61 has three Sau3A sites, one of which is between codons for amino acids 2 and 3. A synthetic HindIII site was inserted 59 nucleotides 3'- of the coding region, and the resulting construct was subjected to a HindIII/partial Sau3A digest. A 560 bp fragment was isolated from the digest. This fragment and a 120 bp EcoRI to Sau3A *E. coli* promoter fragment were ligated together in a three way directed ligation into the EcoRI to HindIII site of pBW11. The promoter fragment contained a synthetic HindIII restriction site, ATG initiation codon, the initial cysteine codon (TGT) common to all known IFN-αs, and a Sau3A "sticky end." The ligation mixture was used to transform *E. coli* MM294 (Backman, K., et al., *Proc Natl Acad Sci (USA)* 73:4174-4178 (1961)). The desired correct transformation products, 8 out of 24 screened, were identified by restriction enzyme mapping of colonies which hybridized to a $^{32}$p-labelled IFN-α genomic fragment. FIG. 12 is a diagram of the final expression plasmid obtained, which is designated pGW20. Other prokaryotic hosts such as bacteria other than *E. coli* may, of course, be transformed with this or other suitable constructs to replicate the IFN-α61 gene and/or to produce IFN-α61.

IFN-α76

The IFN-α76 is a polypeptide having interferon activity and comprising the amino acid sequence:

| | | | |
|---|---|---|---|
| CysAspLeuProGln | ThrHisSerLeuGly | AsnArgArgAlaLeu | IleLeuLeuAlaGln |
| MetGlyArgIleSer | HisPheSerCysLeu | LysAspArgHisAsp | PheGlyPheProGlu |
| GluGluPheAspGly | HisGlnPheGlnLys | AlaGlnAlaIleSer | ValLeuHisGluMet |
| IleGlnGlnThrPhe | AsnLeuPheSerThr | GluAspSerSerAla | AlaTrpGluGlnSer |
| LeuLeuGluLysPhe | SerThrGluLeuTyr | GlnGlnLeuAsnAsp | LeuGluAlaCysVal |
| IleGlnGluValGly | ValGluGluThrPro | LeuMetAsnGluAsp | SerIleLeuAlaVal |
| ArgLysTyrPheGln | ArgIleThrLeuTyr | LeuThrGluLysLys | TrySerProCysAla |
| TrpGluValValArg | AlaGluIleMetArg | SerLeuSerPheSer | ThrAsnLeuGlnLys |
| ArgLeuArgArgLys | Asp | | |

The DNA unit or fragment has the following nucleotide sequence that encodes the IFN-α76 polypeptide:

| TGT | GAT | CTG | CCT | CAG | ACC | CAC | AGC | CTG | GGT | AAT | AGG | AGG |
|---|---|---|---|---|---|---|---|---|---|---|---|---|

-continued

| | | | | | | | | | | | | |
|---|---|---|---|---|---|---|---|---|---|---|---|---|
| GCC | TTG | ATA | CTC | CTG | GCA | CAA | ATG | GGA | AGA | ATC | TCT | CAT |
| TTC | TCC | TGC | CTG | AAG | GAC | AGA | CAT | GAT | TTC | GGA | TTC | CCC |
| GAG | GAG | GAG | TTT | GAT | GGC | CAC | CAG | TTC | CAG | AAG | GCT | CAA |
| GCC | ATC | TCT | GTC | CTC | CAT | GAG | ATG | ATC | CAG | CAG | ACC | TTC |
| AAT | CTC | TTC | AGC | ACA | GAG | GAC | TCA | TCT | GCT | GCT | TGG | GAA |
| CAG | AGC | CTC | CTA | GAA | AAA | TTT | TCC | ACT | GAA | CTT | TAC | CAG |
| CAA | CTG | AAT | GAC | CTG | GAA | GCA | TGT | GTG | ATA | CAG | GAG | GTT |
| GGG | GTG | GAA | GAG | ACT | CCC | CTG | ATG | AAT | GAG | GAC | TCC | ATC |
| CTG | GCT | GTG | AGG | AAA | TAC | TTC | CAA | AGA | ATC | ACT | CTT | TAT |
| CTA | ACA | GAG | AAG | AAA | TAC | AGC | CCT | TGT | GCC | TGG | GAG | GTT |
| GTC | AGA | GCA | GAA | ATC | ATG | AGA | TCC | CTC | TCG | TTT | TCA | ACA |
| AAC | TTG | CAA | AAA | AGA | TTA | AGG | AGG | AAG | GAT. | | | |

Figure 13:
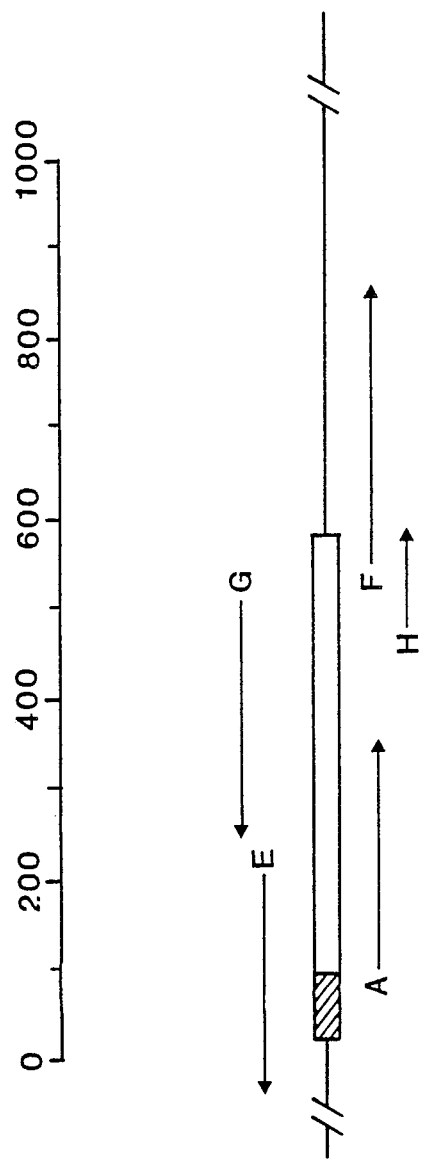
FIG. 13 depicts the sequencing strategy used to obtain the complete DNA sequence of the IFN-$\alpha$76 gene coding region.

FIG. 13 depicts the sequencing strategy used to obtain the complete DNA sequence of the IFN-α76 gene coding region. Bacteriophage mp7:α76-1 DNA served as the template for sequences obtained with primers A, H and F, and bacteriophage mp7:α76-2 DNA was the template for sequences obtained with primers E and G. The crosshatched area of the gene depicts the region that encodes the 23 amino acid signal polypeptide, and the open box depicts the region that encodes the mature polypeptide. The scale, in base pairs, is numbered with 0 representing the ATG start codon of preinterferon. The arrows indicate the direction and extent of sequencing with each primer.

FIG. 14 is the nucleotide sequence of the structural gene coding for IFN-α76, including some of the flanking 5'- and 3'-noncoding regions of the gene. The region coding for preinterferon and the mature polypeptide begins with the ATG codon at position 75 and terminates with the TGA codon at position 642.

Figure 15:
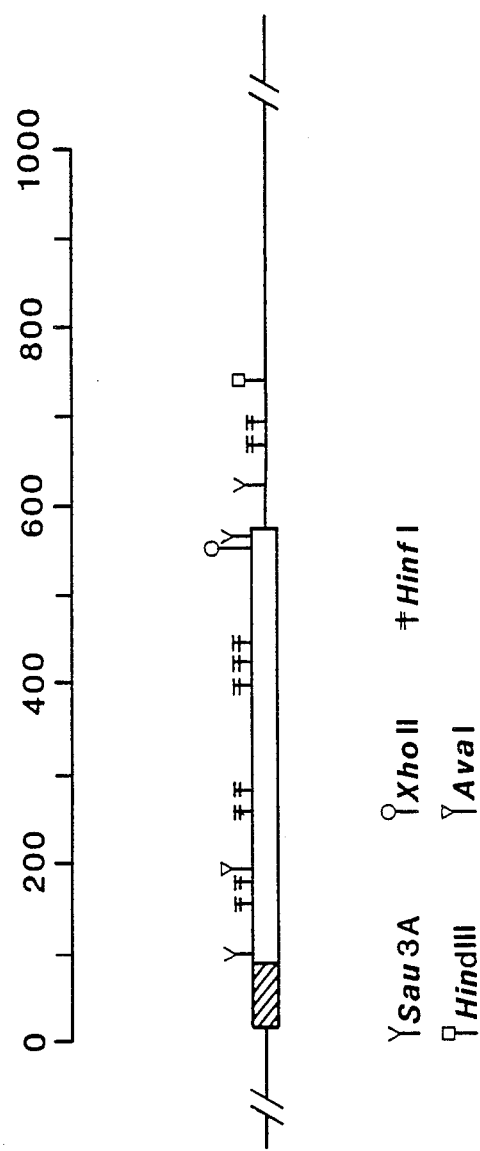
FIG. 15 is a partial restriction map of the coding region of the IFN-$\alpha$76 gene.

FIG. 15 is a partial restriction map of the coding region of the IFN-α76 gene. The crosshatching represents the region that encodes the 23 amino acid signal peptide, and the open box represents the gene coding sequence for the mature polypeptide. The scale, in base pairs, is numbered with 0 representing the ATG start codon of preinterferon.

FIG. 16 shows the amino acid sequence of the 23 amino acid signal polypeptide and the 166 amino acid mature IFN-α76 coded for by the gene depicted in FIG. 14. The 189 amino acid sequence is displayed above the corresponding nucleotide sequence. Amino acid 24, cysteine, is the first amino acid of mature IFN-α76 protein.

FIG. 17 is the DNA sequence of the E. coli trp promoter and the gene of FIG. 14 which was inserted between the EcoRI and HindIII sites of the plasmid pBR322. The amino acid sequence of FIG. 16 is written above the corresponding DNA sequence and the location of the restriction sites used in the construction of the expression plasmid is indicated.

Figure 18:
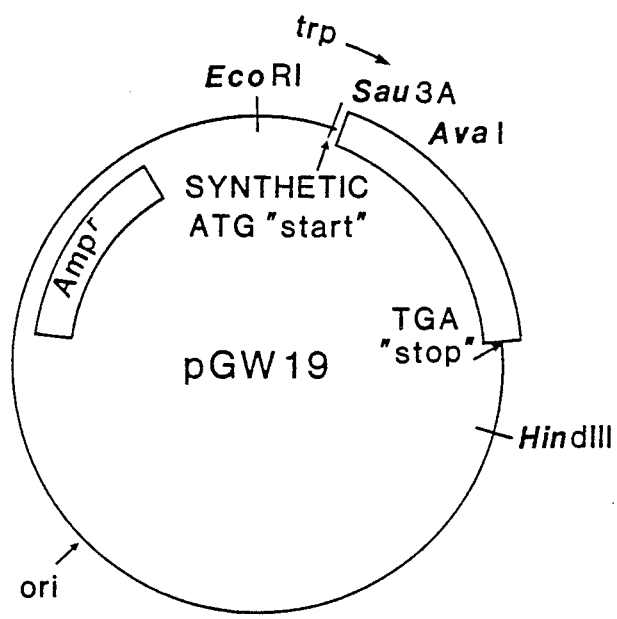
FIG. 18 is a diagram of the expression plasmid, pGW19, used to produce IFN-$\alpha$76.

FIG. 18 is a diagram of the expression plasmid, pGW19.

In general terms, IFN-α76 was made by identifying and isolating the IFN-α76 gene by screening a library of human genomic DNA with an appropriate IFN-α DNA probe, constructing a vector containing the IFN-α76 gene, transforming microorganisms with the vector, cultivating transformants that express IFN-α76, and collecting IFN-α76 from the culture. An embodiment of this procedure is described below.

The preparation of the DNA "260 probe" was the same as that described above for producing IFN-α61.

Screening of Genomic DNA Library for IFN-α76 Gene

One of the 160 clones which hybridized with the $^{32}$P-labeled 260 probe as described above for preparation of IFN-α61 was hybrid phage λ4A:α76 containing a 15.5 kb insert, and was characterized as follows. A DNA preparation of λ4A:α76 was cleaved with HindIII, BglII, and EcoRI, respectively, and the fragments were separated on an agarose gel, transferred to a nitrocellulose filter (Southern, E. M., *J Mol Biol*, 98:503–517 (1977)) and hybridized with $^{32}$P-labeled 260 probe. This procedure localized the IFN-α76 gene to a 2.0 kb EcoRI restriction fragment, which was then isolated and recloned, in both orientations, by ligation of the fragment into EcoRI cleaved M13:mp7. The two subclones are designated mp7:α76-1 and mp7:α76-2. The −1 designation indicates that the single-stranded bacteriophage contains insert DNA complementary to the mRNA (the minus strand) and the −2 designation indicates that the insert DNA is the same sequence as the mRNA (the plus strand).

Sequencing of the IFN-α76 Gene

The Sanger dideoxy-technique was used to determine the DNA sequence of the IFN-α76 gene. The strategy employed is diagrammed in FIG. 13, the DNA sequence thus obtained is given in FIG. 14, and a partial restriction enzyme map of the IFN-α76 gene is illustrated in FIG. 15. Unlike many genes from eukaryotic organisms, but analogous to other IFN chromosomal genes which have been characterized, the DNA sequence of this gene demonstrates that it lacks introns. Homology to protein sequence information from these known IFN-α genes made it possible to determine the correct translational reading frame and thus allowed the entire 166 amino acid sequence of IFN-α76 to be predicted from the DNA sequence as well as a precursor segment, or signal polypeptide, of 23 amino acids (FIG. 16).

The DNA sequence of the IFN-α76 gene and the amino acid sequence predicted therefrom differ substantially from the other known IFN-α DNA and IFN-α amino acid sequences. Nagata, S. et al. (*J Interferon Research*, 1:333–336 (1981)) describe isolating two IFN-α genes, IFN-α4a and IFN-α4b, that differ by five nucleotides which entail two amino acid changes in the proteins expressed thereby. The sequence of INF-αb is given in European Patent Application No. 81300050.2. The IFN-α76 structural gene differs from the IFN-α4b gene by five nucleotides which entail four amino acid changes in the corresponding proteins: a single nucleotide change creates an amino acid substitution of alanine for threonine at amino acid number 14 of the mature protein; a double nucleotide change creates an amino acid substitution of alanine for glutamine at amino acid number 19 of the mature protein; a single nucleotide change creates an amino acid substitution of alanine for threonine at amino acid number 51 of the mature protein; and a single nucleotide change creates an amino acid change of glutamate for valine at amino acid number 114 of the mature protein.

Plasmid Preparation and Host Transformation (INF-α76)

Assembly of the plasmid for direct expression of the IFN-α76 gene involved replacing the DNA fragment encoding the 23 amino acid signal polypeptide of preinterferon with a 120 bp EcoRI/Sau3A promoter fragment (*E. coli* trp promoter, operator, and trp leader ribosome binding site preceding an ATG initiation codon) and using the naturally occuring HindIII site, 142 bp 3'- of the TGA translational stop codon, to insert the gene into a vector derived from the plasmid pBR322. The complete DNA sequence of the promoter and gene fragments inserted between the EcoRI and HindIII sites of pBR322 is shown in FIG. 18, which also shows the exact location of relevant cloning sites. Details of the construction are described below.

Figure 19:
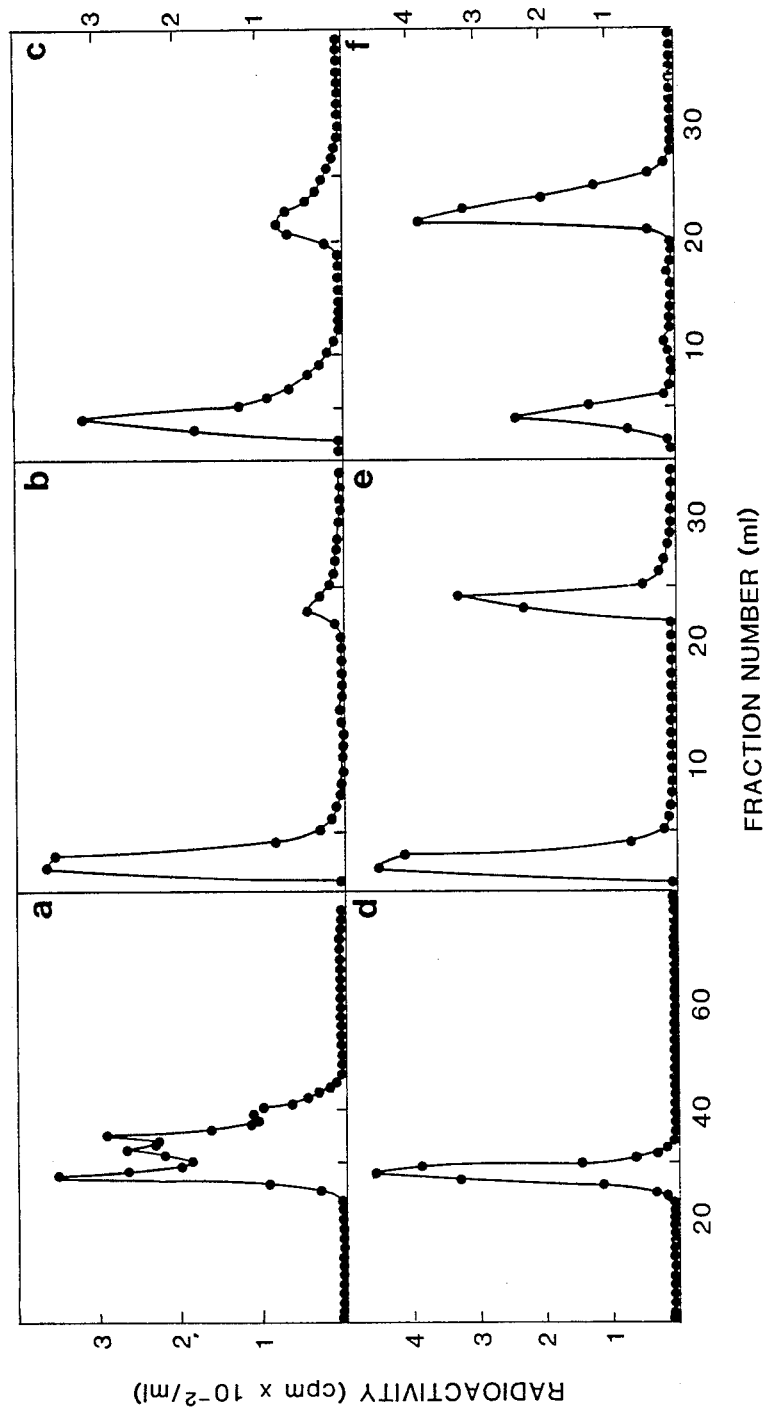
FIG. 19 is a chromatogram of native (a–c) and recombinant CHO-produced (d–f) human $\beta$-interferons showing the heterogeneity of the native material.

The coding region for mature IFN-α76 encompasses a Sau3A site between codons for amino acids 2 and 3 and an AvaI site between codons for amino acids 39 and 40. The 111 bp Sau3A to AvaI fragment was isolated on a 6% polyacrylamide gel following a Sau3A/AvaI double-digest of the 2.0 kb EcoRI genomic fragment. Similarly, the 528 bp fragment from the AvaI site between codons for amino acids 39 and 40 and the HindIII site 142 nucleotides 3'of the translational stop codon was isolated on a 5% polyacrylamide gel. These two fragments, together with a 120 bp EcoRI to Sau3A *E. coli* promoter fragment, were ligated together in a four way directed ligation into the EcoRI to HindIII site of pBR322. The promoter fragment, which contains a synthetic HindIII restriction site, ATG initiation codon, the initial cysteine codon (TGT) common to all known IFN-αs, and Sau3A "sticky end," had been constructed previously. The ligation mixture was used to transform *E. coli* MM294 (Backman, K., et al., *Proc Natl Acad Sci (USA)* 73:4174–4178 (1976)). The desired correct transformant, one out of 24 screened, was identified by restriction enzyme mapping of colonies which hybridized to a $^{32}$P-labelled IFN-α genomic fragment. FIG. 19 is a diagram of the final expression plasmid obtained, which is designated pGW19. Other prokaryotic hosts such as bacteria other than *E. coli* may, of course, be transformed with this or other suitable constructs to replicate the IFN-α76 gene and/or to produce IFN-α76.

Cultivation of Transformants with IFN-α61 or IFN-α76 Gene

Bacteria transformed with the IFN-α61 or IFN-α76 gene may be cultivated in an appropriate growth medium, such as a minimum essential medium, that satisfies the nutritional and other requirements needed to permit the bacteria to grow and produce IFN-α61 or IFN-α76. If the bacteria are such that the protein is contained in their cytoplasm, the IFN-α61 or IFN-α76 may be extracted from the cells by lysing the cells such as by sonication and/or treatment with a strong anionic solubilizing agent such as sodium dodecyl sulfate. Further purification of the extract may be achieved by affinity chromatography, electrophoresis, or other protein purification techniques.

Biological Testing of IFN-α61 and IFN-α76

IFN-α61 - and IFN-α76 - containing cell sonicates were tested in vitro and found to have the following activities: (1) inhibition of viral replication of vesicular stomatitis virus (VSV) and herpes simplex virus-1 (HSV-1); (2) inhibition of tumor cell growth; (3) inhibition of colony formation by tumor cells in soft agar; (4) activation of natural killer (NK) cells; (5) enhancement of the level of 2',5'-oligoadenylate synthetase (2',5'-A); and (6) enhancement of the double-stranded RNA-dependent protein kinase. The sonicates were active in inhibiting viral infection in both human and other mammalian cells such as hamster, monkey, mouse, and rabbit cells.

The tests show that IFN-α61 and IFN-α76 exhibit anti-viral activity against DNA and RNA viruses, cell growth regulating activity, and an ability to regulate the production of intracellular enzymes and other cell-produced substances. Accordingly, it is expected that IFN-α61 and IFN-α76 may be used to treat viral infections with a potential for interferon therapy such as chronic hepatitis B infection, ocular, local, or systemic herpes virus infections, influenza and other respiratory tract virus infections, rabies and other viral zoonoses, arbovirus infections, and slow virus diseases such as Kuru and sclerosing panencephalitis. They may also be useful for treating viral infections in immunocompromised patients such as herpes zoster and varicella, cytomegalovirus, Epstein-Barr virus infection, herpes simplex infections, rubella, and progressive multifocal leukoencephalopathy. Their cell growth regulating activity makes them potentially useful for treating tumors and cancers such as osteogenic sarcoma, multiple myeloma, Hodgkin's disease, nodular, poorly differentiated lymphoma, acute lymphocytic leukemia, breast carcinoma, melanoma, and nasopharyngeal carcinoma. The fact that IFN-α61 and IFN-α76 increase protein kinase and 2',5'-oligoadenylate synthetase indicates that they may also increase synthesis of other enzymes or cell-produced substances commonly affected by IFNs such as histamine, hyaluronic acid, prostaglandin E, tRNA methylase, and aryl hydrocarbon hydrolase. Similarly, they may be useful to inhibit enzymes commonly inhibited by IFNs such as tyrosine amino transferase, glycerol-3-phosphate dehydrogenase glutamine synthetase, ornithine decarboxylase, S-adenosyl-1-methionine decarboxylase, and UDP-N-acetylglucosaminedolichol monophosphate transferase. The ability of the IFN-α61 and IFN-α76 to stimulate NK cell activity is indicative that they may also possess other activities such as the abilities to induce macrophage activity and antibody production and to effect cell surface alterations such as changes in plasma membrane density or cell surface charge, altered capacity to bind substances such as cholera toxin, concanavalin A and thyroid-stimulating hormone, and change in the exposure of surface gangliosides.

Pharmaceutical compositions that contain IFN-α61 or IFN-α76 as an active ingredient will normally be formulated with an appropriate solid or liquid carrier depending upon the particular mode of administration being used. For instance, parenteral formulations are usually injectable fluids that use pharmaceutically and physiologically acceptable fluids such as physiological saline, balanced salt solutions, or the like as a vehicle. Oral formulations, on the other hand, may be solids, e.g. tablet or capsule, or liquid solutions or suspensions.

IFN-α61 and IFN-α76 will usually be formulated as a unit dosage form that contains in the range of $10^4$ to $10^7$ international units, more usually $10^6$ to $10^7$ international units, per dose.

IFN-α61 and IFN-α76 may be administered to humans in various manners such as orally, intravenously, intramuscularly, intraperitoneally, intranasally, intradermally, and subcutaneously. The particular mode of administration and dosage regimen will be selected by the attending physician taking into account the particulars of the patient, the disease and the disease state involved. For instance, viral infections are usually treated by daily or twice daily doses over a few days to a few weeks; whereas tumor or cancer treatment involves daily or multidaily doses over months or years. IFN-α61 and IFN-α76 therapy may be combined with other treatments and may be combined with or used in association with other chemotherapeutic or chemopreventive agents for providing therapy against viral infections, neoplasms, or other conditions against which it is effective. For instance, in the case of herpes virus keratitis treatment, therapy with IFN has been supplemented by thermocautery, debridement and trifluorothymidine therapy.

IFN-β

DNA sequences, encoding human IFN-β, promoter sequences, and translation sequences therefor are described in D. V. Goeddel, et al., *Nuc. Acids Res.* 8, 4057 (1980), in Taniguchi, et al., *Proc. Japan Acad. Sci.* 855, 464 (1979), in European Patent Application No. 81301414.9, and in U.S. Pat. No. 4,518,584 (on muteins of IFN-β).

Process Details

Any promoter sequence, including endogenous or heterologous bacterial or viral promoters, which facilitates the expression of the IFN genes in CHO cells may be employed in operable linkage with the IFN gene. Typical promoters suitable for the practice of this invention include, e.g., SV40 early promoter, HaMSV promoter, MMTV promoter, TK promoter, endogenous IFN promoter, and the like. SV40 early promoter, IFN endogenous promoter, and MMTV promoter are preferred. The interferon gene is also operably linked to suitable start and stop codons which are generally described in the art.

In accordance with the present invention, any approach may be used to introduce the cloned DNA into CHO cells and to select and grow the transformed cells for expression of the protein. Among the approaches for transfection are the following three approaches: The first makes use of the technique of DNA transfection (Graham, F., and van der Eb, A., *Virology* 52, 456–467 (1973)). In this process, purified DNA is precipitated from solution and enters cells in this insoluble form. In a small fraction of the cells, the DNA taken up becomes integrated into the cell genome through a random recombinant event. The cells that have taken up and integrated into the DNA can be selected from the cells which do not use the marker gene. The end result of this protocol is, therefore, a cell line that contains cloned DNA in an integrated form. If the cloned DNA contains appropriate transcriptional promoters, poly(A) addition sites and other regulatory elements, expression of functional mRNA can be achieved.

The second approach for introducing cloned DNA into CHO cells takes advantage of the fact that animal viruses penetrate cell membranes extremely efficiently, and afford a means of delivering DNA to the cell nucleus where it can be replicated to a high copy number and thus expressed at high levels. Cell death occurs within a few days of infection of cells with DNA viruses such as papova virus (e.g., SV40, polyoma virus) and adenovirus. However, in this period, sufficient quantities of viral gene products are synthesized to permit biochemical analysis. Cloned DNA has been inserted into the genomes of several DNA viruses, and it has been shown that this DNA can direct synthesis of high levels of active proteins. Furthermore, infectious virus is produced that can be used as a vector to transport the cloned gene into other cells for repeated cycles of expression. SV40 is the virus of choice. The advantages of this approach over DNA transfection/selection are that high levels of expression can be achieved in a short period of time. The virus can be used to infect various cell lines, and the genes can be recovered and examined. This method is used to characterize genetic elements involved in regulation of gene expression.

A third approach involves transfection of cloned plasmids into cells that express SV40 regulatory proteins (T-antigens). Plasmids that contain SV40 DNA origin fragments are replicated to a high copy number in these cells (COS cells), and genes encoded by the plasmid DNA can be expressed at significant levels, if the gene contains appropriate promoters and regulatory elements. The use of the SV40 origin compensates to some extent for the low efficiency at which DNA enters cells by transfection. The advantage of this technique is that plasmids containing cloned genes or cDNA copies can be screened very quickly for expression of active gene products. The cloned gene does not have to be engineered into SV40 DNA for expression. The limitation of the technique is that it does not lead to production of a stable cell line or recombinant virus stock that can be used for further studies. It is used for testing the expression capacity of plasmids prior to introducing the cloned DNA into cells or a virus genome.

The transformed cells are then selected by growing them in a selection medium to which the marker gene is not resistant, under conditions whereby the interferon gene is expressed, by techniques well known in the art.

After growth of the selected transformed cells, mutant cell lines are selected from the growth media which are resistant to the negative growth effects (e.g., antiproliferative effects) of human interferon. Thus, above a certain level of expression, the human interferon is toxic to the host cells which are not selected to be resistant. By such selection, one can achieve high levels of human interferon expression.

The IFN so expressed is secreted into the medium wherefrom it can be isolated and purified by any conventional means known to those skilled in the art. The methods for isolation and purification used in the preferred embodiment are immunoprecipitation, gel electrophoresis and chromatographic techniques.

The IFN products obtained are useful as therapeutic agents individually or as mixtures in the control of cancer, psoriasis, and viral diseases and as immunoregulatory agents. See the above discussion regarding IFN-α61 and IFN-α76. They may be formulated in any therapeutically and pharmacologically acceptable carrier medium such as distilled water, physiological saline, Ringer's solution, Hank's solution and the like, and may be administered orally or parenterally.

The following examples are presented to assist in the better understanding of the subject invention and are not to be construed as limiting the scope of the invention in any manner. In these examples, all parts and percentages for solids are by weight and for liquids and gases are by volume, and all temperatures are in degrees Celsius unless otherwise indicated.

EXAMPLE 1

Cells and DNA Transformation:

CHO cells deficient in dihydrofolate reductase (dhfr, Urlaub, G. and Chasin, L. S., *Proc. Natl. Acad. Sci.* 77, 4216–4220 (1980)) were grown in Ham's F12 medium supplemented with 4% newborn and 4% fetal calf serum. CHO cells containing dhfr activity were grown in Dulbecco's Modified Eagle's (DME) medium supplemented with 8% fetal calf serum and 35 μg/ml proline. DNA transfections were carried out as described by Ringold et al., *J. Molec., App. Genetics* 1, 16514 175 (1982).

Interferon Induction and Assay:

Human IFN-$\beta_1$ (hIFN-$\beta_1$) was induced by addition of poly (rI).(rC)(20 μg/ml) and cycloheximide (2 μg/ml) to confluent monolayers for 3 hr at 37° C. Cells were rinsed twice with phosphate buffered saline (PBS) and exposed to medium containing actinomycin D (2 μg/ml) for 1 hour, rinsed again and given fresh medium. After 18–24 hours, the medium was harvested and stored at 4° C., or frozen at −20° C. IFN-$\beta$ was induced by infecting confluent cells with $10^8$ pfu of Newcastle Disease virus (NDV) (Manhattan strain) for 24 hours at 37° C. Supernatants were harvested and the pH was adjusted to 2.0 to inactivate virus. After 4 days at 0° C. the pH was readjusted to 7.0.

For the IFN assay, samples were diluted to a volume of 75 μl in Modified Eagle's Medium (MEM) and diluted serially in microtitre wells and sterilised by irradiation with UV light. A total of $1.2 \times 10^5$ human fibroblast cells (GM-2504) was added to each well followed by one plaque-forming unit of VSV and cytopathic effect (CPE) scored after 18–24 hours. The titer was estimated relative to NIH IFN-$\gamma$ or IFN-$\beta$ standards.

Construction of hIFN DNA Transducing Vectors

The vectors used were derivatives of plasmids pSV2-dhfr or pSVM-dhfr, which are derivatives of pBR322 and which contain the mouse dihydrofolate reductase (DHFR) gene under the direction of a promoter derived from SV40 and the mouse mammary tumor virus (MMTV), respectively.

The gene for hIFN-$\beta_1$ was isolated from a 17 kb human genomic DNA insert cloned into Charon 4A. A 1.8 kb EcoR1 fragment of this clone has been characterized and sequenced (Ohno, S. and Taniguchi, T., *Proc. Natl. Acad. Sci.* 78, 5305–5309 (1981)) and shown to contain the entire transcribed region as well as 243 and 714 nucleotides in the 5' and 3' flanking noncoding sequences, respectively. The plasmid pMI7 was constructed as follows. The 1.8 kb hIFN-$\beta_1$ DNA fragment was isolated by EcoR1 cleavage of clone C15 followed by agarose gel electrophoresis. The purified 1.8 kb fragment was ligated into the unique EcoR1 site of pSVM-dhfr and transformed into *E. coli*. The resulting recombinant plasmids were screened by restriction enzyme analysis. The structure of pMI-7 is shown in FIG. 1. Transcription from both the MMTV promoter and the hIFN-$\beta_1$ promoter is shown in counterclockwise direction.

Figure 2:
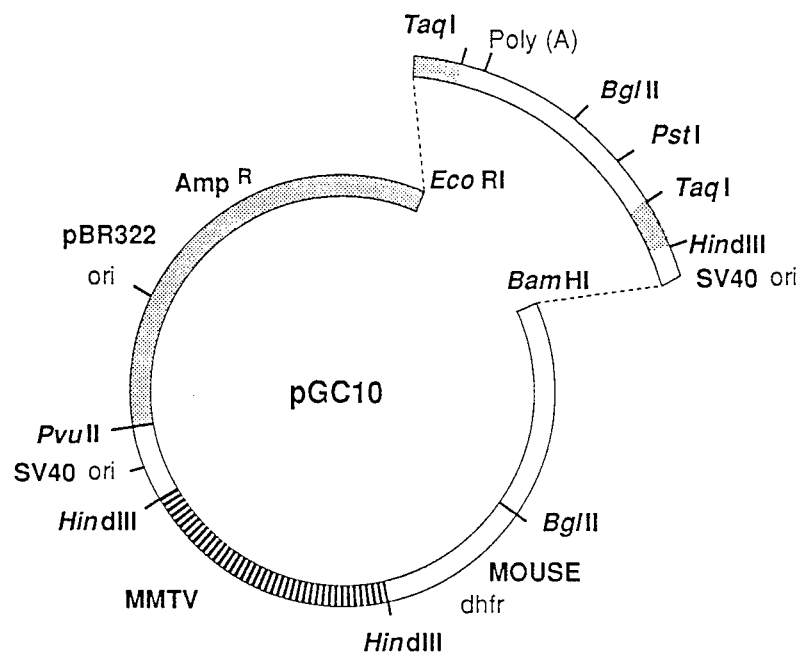
FIG. 2 shows a diagram of plasmid pGC10 containing the human IFN-$\beta$ gene and some 3' flanking noncoding sequences fused to SV40 early promoter sequence.

The plasmid pGC10 contains the structural gene and some 3' flanking sequences of hIFN-$\beta_1$ fused to the heterologous SV40 early promoter and inserted between BamHI and EcoRI sites of pSVM-dhfr. This was accomplished in several steps. First, plasmid pGR1 was constructed by cloning a 340 bp BamHI adapted-PvuII to HindIII fragment that encodes the SV40 origin and early promoter between the BamHI and HindIII sites of pBR322. Next, the 838 bp TaqI fragment of the hIFN-$\beta_1$ gene which contains 55 nucleotides of the 5'untranslated leader, the structural gene including the poly(A) addition signal, and 18 nucleotides of 3'flanking sequence was isolated by electrophoretic separation and cloned into the ClaI site adjacent to the HindIII site of pGR1. Recombinant clones in the correct orientation were identified by restriction enzyme analysis. The fused gene was excised by EcoR1/BamHI digestion and cloned between the BamHI and EcoR1 sites of pSVM-dhfr. The transcription of hIFN-$\beta_1$ by the SV40 promoter occurs in the counterclockwise direction. The structure of pCG10 is shown in FIG. 2.

Figure 3:
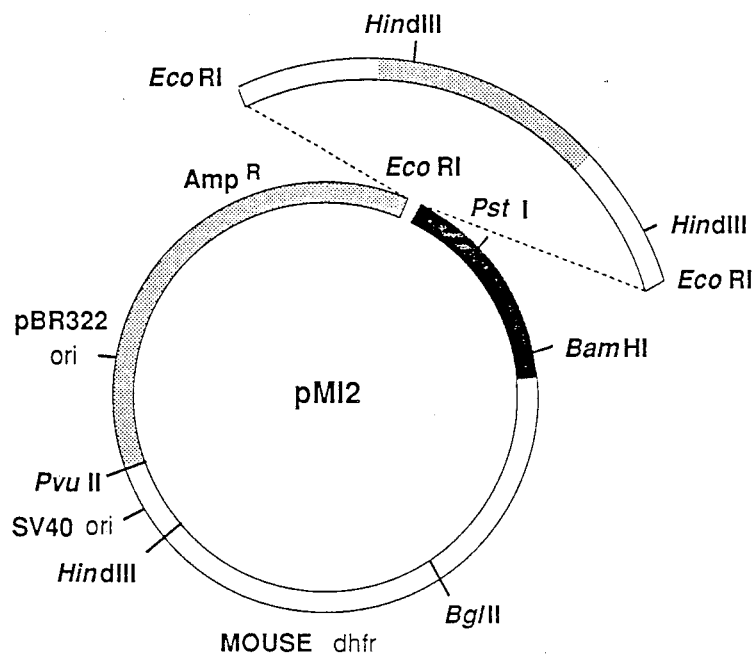
FIG. 3 is a diagrammatic representation of plasmid pM12 containing human IFN-$\alpha$ gene.

The plasmid pMI2 contains an alpha interferon chromosomal gene, termed IFN-$\alpha$76, inserted into the EcoRI site of pSV2-dhfr. The IFN-$\alpha$76 gene resides on a 1.95 kb EcoRI fragment and is flanked by 710 nucleotides at the 5'end and 300 nucleotides at the 3'end of the gene. The 1.95 kb EcoRI fragment was isolated and cloned into the EcoRI site of pSV2-dhfr. The structure of pMI2 is shown in FIG. 3. Transcription of the IFN-$\alpha$76 gene occurs counterclockwise.

Figure 4:
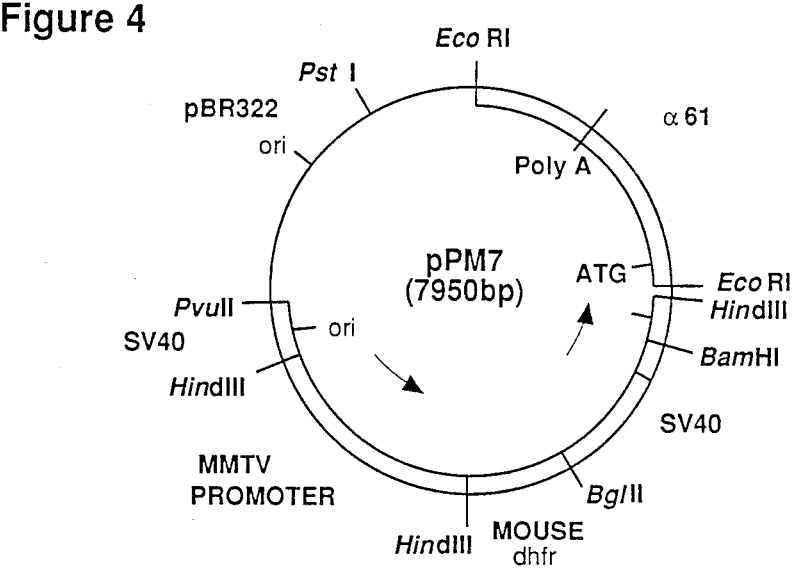
FIG. 4 shows a diagram of plasmid pPM7 containing IFN-$\alpha$ gene fused to SV40 early promoter sequence.

The plasmid pPM7 containing an alpha interferon chromosomal gene, described as IFN-$\alpha$61, was fused to the heterologous SV40 early promoter fragment and was inserted between the EcoRI and BamHI sites of pSVM-dhfr. The IFN-$\alpha$61 gene was isolated from a human gene library and subcloned as a 1.87 kb BglII fragment into the BamHI site of M13:mp7. The BglII fragment contained the transcribed region of IFN-$\alpha$61, 27 nucleotides of the 5'end of the transcribed region not including a promoter and 840 nucleotides from the 3'flanking sequences. The BglII fragment of IFN-$\alpha$61 was excised from the M13:mp7 subclone using the flanking EcoRI sites of M13:mp7, purified by electrophoretic separation and cloned into the EcoRI site of pGR1 adjacent to the SV40 promoter. Clones in the correct orientation were identified by restriction mapping, and the fused gene was transferred to pSVM as a PstI/BamHI fragment exchange. The structure of pPM7 is shown in FIG. 4. Transcription of the IFN-$\alpha$61 gene by the SV40 promoter is shown in the counterclockwise direction.

Levels of IFN Expression from Transformed CHO Cells

The plasmids described above were transfected into dhrf-CHO cells, and transformants selected and cloned levels of IFN produced constitutively or on induction were determined. The results of these assays are presented in Table 1.

TABLE 1

EXPRESSION LEVELS OF HUMAN INTERFERON IN CHINESE HAMSTER OVARY CELLS

| CHO CELL LINE | IFN | PROMOTER | IFN (U/ml)[1] CONSTITUTIVE | SUPER INDUCTION[3] | NDV[4] |
|---|---|---|---|---|---|
| MI2.2 | α76 | own | 10 | 100 | 300 |
| PM7 | α61 | SV40 | 1000 | 1000 | not done |
| GC10 | β1 | SV40 | 100 | 100 | 100 |
| MI7.1 | β1 | own | 100 | 10,000 | 1000 |
| MI7.1.R10[2] | β1 | own | 1000 | 30,000 | — |
| MI7.1.R10 (roller bottle) | β1 | own | 10,000 | 600,000 | — |

[1]IFN(U/ml) relative to NIH α or β standards on human GM2504 cells with VSV challenge.
[2]MI7.1.R10 is a subclone of MI7.1 resistant to 10nM methotrexate.
[3]Superinduction: cells were aged 2 days post confluence, then incubated in fresh medium containing 20 μg/ml poly(I) · poly(C) and 2 μg/ml cycloheximide for 3 hrs. at 37° C.; actinomycin D was then added (2 μg/ml) and cells were incubated 1 hr. at 37° C.; monolayers were washed 3× and fresh medium was replenished; cells were incubated at 37° C. and supernatants harvested 24 hrs. later.
[4]NDV induction: cells were grown to confluency, then incubated in fresh medium containing 1/5 volume NDV Manhattan strain (titer-5.5 × 10[8]) for 24 hrs. at 37° C.; supernatants were harvested, pH was adjusted to 2.0 and supernatant was placed at 0° C. for 4 days; pH was readjusted to 7.0 prior to assay.

In each case, the species of IFN produced was identified by its ability to be neutralized by either bovine anti-human leukocyte IFN antiserum or by rabbit anti-human β1 antiserum. Supernatants were also assayed for hamster IFN production on BHK cells; no hamster IFN could be detected under the assay conditions used.

α-76 was expressed constitutively at low levels from CHO.MI2.2 cells. This level was increased by poly(rI):poly(rC) superinduction, and by infection with NDV. The latter induction protocol was more effective. α-76 from CHO.MI2.2 was also assayed on MDBK cells (a bovine kidney cell line). Its activity on these cells was comparable to its activity on human fibroblasts (GM2504). An α gene (α-61) expressed from the SV40 early promoter could not be induced by poly (rI):poly(rC), as shown in Table 1.

IFN-α1 was secreted constitutively using either the SV40 early promoter (CHO.GC10) or its own promoter (CHO.MI7.1). However, expression could only be induced in the latter case. Higher levels of expression were obtained from a poly(rI):(rC) superinduction protocol than with NDV, as in the case of human fibroblast IFN. A derivative of CH).MI7.1 was selected for its ability to grow in the presence of 10 nM methotrexate (a folate analog). These cells (CHO.MI7.1.R10) produced ten times more IFN-β1 constitutively than the parental line, and three to ten times more on superinduction. Southern blotting analysis indicated that this increased expression may be due, in part, to increased copy number of DNA coding for IFN-β1 in these cells.

IFN-β, produced by CHO.MI7.1.R10 was labeled metabolically using $^{35}$S-methionine (100 μCi/ml) for 18 hours after medium change or superinduction. One ml of the secreted supernatant was incubated with 10 μ of rabbit antiserum raised against purified E. coli β-IFN for 2 hours at 25° C. Immune complexes were precipitated with Staph A, eluted with 2% SDS, O.M.I. DTT and run on 15% SDS-PAGE, [and the secreted product was immunoprecipitated from culture supernatants using antibody raised against E. coli produced IFN-β. The results are shown in FIG. 6.] Two major polypeptides were observed that were present in induced, but not uninduced, supernatants. These had apparent molecular weights of 23 Kd and 18.5 Kd, and correspond to glycosylated and unglycosylated forms of IFN-β1, respectively.

In order to determine the effect of extraneous factors on the production of IFN-β from CHO cells, the superinduction protocol was varied as shown below.

TABLE 2

| Induction Protocol | | | IFN Titre (U/ml) after 24 Hours |
|---|---|---|---|
| poly (rI) · poly (rC) + | CHI, | Act D. | 30,000 |
| poly (rI) · poly (rC) + | CHI | — | 3,000 |
| poly (rI) · poly (rC) | — | — | 300 |
| — | CHI, | Act D. | 300 |
| — | CHI | — | 100 |
| — | — | Act D. | 1,000 |
| — | — | — | 100 |
| poly (rI) · poly (rC), | rinse, | CHI, Act D. | 300 |

The results obtained showed that poly (rI).(rC) was relatively ineffective when added alone. However, in the presence of the translation inhibitor cycloheximide (CHI) as well as poly (rI).(rC), a 30-fold induction was observed over the control with no induction protocol. When CHI was added after the addition of poly (rI).poly(rC), its enhancing effect was lost. Furthermore, addition of actinomycin D resulted in a further ten-fold increase in induction.

Figure 5:
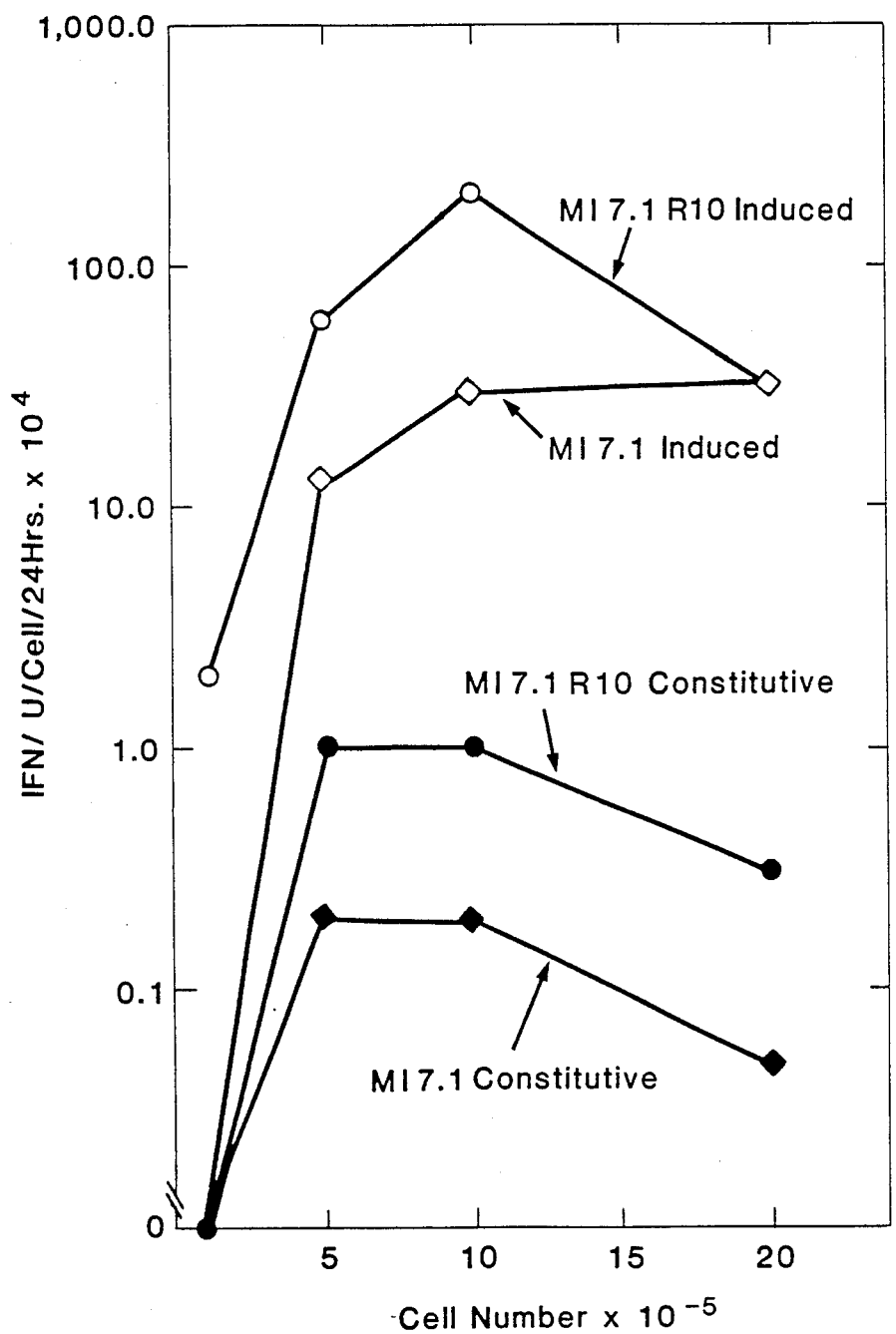
FIG. 5 is a graph showing levels of IFN production as a function of cell density.

FIG. 5 shows the effects of cell density on production of IFN-β1 from CHO.MI7.1 and the methotrexate derivative CHO.MI7.1.R10. Results are presented as IFN production per cell, and it can be seen that the efficiency of production was highly dependent on cell density. Thus, a 10-fold increase in cell density could result in a 100-fold increase in IFN production. Similar results were obtained when cells were maintained in the presence of neutralizing antibody before induction. The superinduction yielded 600,000 U/ml IFN from CHO.MI7.1.R10 grown to high cell density in roller bottle cultures. This is equivalent to $10^9$ U from 20 roller bottles.

EXAMPLE 2

This example illustrates the differences between the recombinant interferon-β from CHO cells of this invention and diploid human fibroblasts.

Human IFN-α secreted by recombinant CHO cells (CHO.M17.R301000) or by diploid human fibroblasts obtained from the CTT2 strain deposited with the American Type Culture Collection of Rockville, Md., (ATCC) both have been found to exist as a glycosylated form (apparent molecular weight of 23,000) and an unglycosylated form (apparent molecular weight of 18,500). These forms are described by McCormick et al., *Mol. Cell. Biol.*, 4:166-172(1984) in detail.

Labeling with Tritiated Mannose

For further characterization of the two species, both the recombinant and native IFN-β described above were labeled with mannose. For the recombinant IFN-β a confluent 100 mm dish of CHO.MI7.R30-1000 cells prepared as described in Example 1 was superinduced as described in Example 1. CHO.MI7.R30 -1000 cells are a subclone of MI7.1 which are resistant to 30 nM to 1000 nM methotrexate. After superinduction, the cells were washed in phosphate buffered saline and labeled for one hour in glucose-free, serum-free medium containing 5 μCi/ml of 2-$^3$H mannose (27.2 Ci/mmole, from ICN Radiochemicals). Labeled medium was collected and the cells were incubated for a further four hours in serum-free medium. These labeled medium samples were pooled and dialyzed against 1/100×gel sample buffer as described by McCormick et al., supra, and were concentrated 100-fold for loading for SDS-PAGE analysis. The unfixed gel, containing radioactive protein markers, was exposed for autoradiography overnight and gel slices were removed in the region between 20,000 and 30,000 kdaltons. The human diploid fibroblast cells of the CTT2 strain from ATCC were induced as described by McCormick et al., supra, and were washed, labeled, pooled, dialyzed, and concentrated for loading as described for the recombinant IFN-β.

SDS-PAGE gel separation, followed by elution from gel slices, was used to purify the mannose-labeled IFN-β from both induced supernatants. Radiolabeled material was eluted from the gel in the region corresponding to 20-30,000 daltons, and eluted material was analyzed for IFN-β activity and TCA-precipitable radioactivity. Medium from 2-$^3$H mannose labeled cells was found to contain $5 \times 10^5$ TCA-precipitable c.p.m. per ml. This medium was concentrated by centrifugation under vacuum and IFN-β was separated by SDS PAGE. Gel slices were protein eluted. The eluates were analyzed for antiviral activity by the method described by McCormick et al., supra, and for TCA-precipitable material. These two properties were both found in the peak material corresponding to 23,000 daltons for both human diploid fibroblast and CHO cell-derived material.

Comparison of Glycans Carried by Recombinant and Native IFN-β

In the next step of the analysis wherein the glycopeptides are compared, the labeled recombinant IFN-β and native IFN-β induced as already discussed above were exhaustively digested with pronase to produce glycopeptides and then with endo-H to release any high-mannose glycans as follows, with the results illustrated in FIG. 19: The interferons were separately solubilized from SDS polyacrylamide gels in 50 mM NH$_4$HCO$_3$, 0.1% SDS, and 5% 2-mercapto-ethanol, 10 mM of calcium salt was added thereto, and the resulting material was centrifuged. The supernatant was dried and resuspended in 0.5 ml of a 1% pronase solution and incubated with a toluene overlay at 55° C. Additional 0.5-ml aliquots were added at 24 and 48 hours and the total length of the digestion was 72 hours. The digestion products were boiled for 10 minutes, acidified to pH 5.5 with acetic acid and incubated for two days with 10 mU of endo-H for 48 hours at 37° C.

FIG. 20 shows the results, where (a-c) represent the properties of glycans from native human IFN-β, and (d-f) represent the properties of glycans from recombinant HIFN-β. The digestion products were fractionated on 80 ml gel filtration columns consisting of 1.3×100 cm of Bio-Gel P4 (Bio-Rad Laboratories) of minus 400 mesh (FIG. 20, a and d). The column was eluted with 200 mM ammonium acetate, pH 7.0, containing 0.05% NaN$_3$, at a flow rate of 4 ml/hour. One-milliliter fractions were collected.

High mannose glycans eluted between fractions 55 and 65. Complex-type glycans included in the matrix being subjected to gel filtration eluted between fractions 30-48, where those with 2, 3 and 4 sialyllactosamine branches eluting at fractions 32, 36 and 40, respectively, and biantennary complex-type glycans with 2, 1, and 0 sialic acids eluting at fractions 40, 44 and 48, respectively. Unexpectedly, all of the glycans carried by the recombinant IFN-β were excluded from this matrix. The glycans carried by native IFN-β were a mixture of glycans eluting between fractions 26–44. Unfractionated glycopeptides were also chromatographed on Sepharose immobilized pokeweed mitogen (FIG. 19, b and e), and Sepharose immobilized agglutinin from *Canavalia ensiformis* (Con A) from Sigma Chemical Co. (FIG. 19, c and f). Samples were applied in 1 ml of phosphate buffered saline (PBS) and the columns were washed with 20 ml PBS. Immobilized pokeweed mitogen was then eluted with 20 ml of 0.2 M Na$_2$B$_4$O$_7$ in 0.02 M NaOH. Material displaced by this solution was, after dialysis against PBS, still retained by immobilized pokeweed mitogen. Immobilized Con A was then eluted with 20 ml of 25 mM α-methylmannoside in PBS. No further material was eluted from immobilized Con A by subsequent 20-ml washes with 200 mM α-methylmannoside in PBS or 0.2 M Na$_2$B$_4$O$_7$ in 0.02 M NaOH. The glycans carried by native IFN-β differ from those of recombinant IFN-β in their affinities for pokeweed mitogen and Con A. Very few of the glycans from native IFN-β were retained by either lectin, in comparison to the glycans from recombinant IFN-β.

The following analyses demonstrate that a large fraction (about 40%) of the native glycans are very similar to the recombinant glycans and that native glycans contain, in addition, small complex-type glycans which are the more common fibroblastic glycans.

Large Versus Small Glycans

The designation of glycans excluded by Bio-GelP4 as "large" was not arbitrary, as the following enzyme digestions demonstrate. Glycopeptides from native IFN-β were fractionated on a mixed bed column of 1.3×100 cm of Bio-Gel P4 (upper 60 cm of column packing) and Bio-Gel P10 (lower 60 cm of column packing, from Bio-Rad) into material included in the original Bio-Gel P4 column (63%) and excluded material. Prior to rechromatography of these materials, some of the included and excluded materials were treated with 0.5 U neuraminidase (*Clostridium perfringens*) from Sigma Chemical Co., in 0.1M citrate, pH 5.5 at 37° C. for 4 hours under a tolune overlay. Some of the excluded material was treated with endo-β-galactosidase from Dr's. Minoru and Michiko Fukuda, La Jolla Cancer Research Foundation, by adding the material to a buffer of 0.1M citrate pH 5.8 containing a 10-U aliquot of the enzyme, to which 10-U aliquots of the enzyme were added every 24 hours for a total of 72 hours. Incubation was performed at 37° C. with 0.05% (w/w) NaN₃ added to inhibit bacterial growth. A portion of the unfractionated glycans from recombinant IFN-β was also treated with endo-β-galactosidase. The gel filtration columns were eluted as described above for gel filtration.

The results show that there was a substantial decrease in the apparent size of the native glycans on desialylation. The major peak of desialylated material corresponded in size to a complex-type fibroblast standard having three N-acetyllactosamine antennae. In contrast, the bulk of the native glycans originally excluded from Bio-Gel P4 were still eluted near the exclusion limit after neuraminidase digestion. However, these glycans, like the recombinant glycans, are extensively depolymerized by endo-β-galactosidase, which selectively hydrolyzes polymers containing repeating GlcNAcβ1-3Galβ1'-4 0 sequences. These various enzyme digestions reduce the previously excluded and included native glycans to similarly sized core structures. While the cores of the small glycans are decorated with sialic acid, the core of the large glycans is extended with repeating sequences of galactose and N-acetylglucosamine.

The similarities between the excluded glycans from native and recombinant β-interferons and the differences between the excluded and included native glycans are shown by the following analysis.

Comparison of the Core Regions of Native and Recombinant Glycans

Glycans from native β-interferon were fractionated into large (37%) and small (63%) glycans by gel filtration on Bio-Gel P4 as described above. These two classes of glycans and the unfractionated glycans from recombinant β-interferon were then analyzed by sequential lectin affinity chromatography. The results of this fractionation are shown in Table 3, where PWM is immobilized pokeweed mitogen, Pea is Sepharose-immobilized pea lectin from Sigma Chemical Co., and E-PHA and L-PHA are erythro- and leuko- phytohemagglutinins, respectively, immobilized on Sepharose and obtained from E-Y Laboratories.

In this process the glycans were subjected to affinity chromatography on 1 ml columns of the immobilized lectins. The glycans were dissolved in PBS and applied to the columns at a flow rate of 0.25 ml/min. Con A and Pea were eluted with 10 ml PBS and then with 10-ml aliquots of PBS containing 25 mM and 200 mM α-methylmannoside. PWM was eluted with 20 ml PBS and then with 20 ml 0.2M Na₂B₄O₇ in 0.02 M NaOH. E-PHA and L-PHA were eluted with 20 ml of PBS. The predominant small glycans have a tri-antennary arrangement with no core fucosylation and carry either two or three sialic acids. The glycans carried by recombinant interferon molecules are unusual both in their carbohydrate structures and in the fact that they represent only a minor subset of the glycans expressed by native fibroblastic cells.

TABLE 3

The Lectin Binding Properties of the Glycans Carried by Native and Recombinant β-Interferons

| Lectin | | | Recombinant Glycans | Native Glycans Large | Small |
|---|---|---|---|---|---|
| PWM | − | (I) | 62 (62) | 72 (26) | 100 (63) |
| | + | (II) | 38 (38) | 28 (11) | − (—) |

TABLE 3-continued

The Lectin Binding Properties of the Glycans Carried by Native and Recombinant β-Interferons

| Lectin | | | Recombinant Glycans | Native Glycans Large | Small |
|---|---|---|---|---|---|
| Con A | − | (III) | 29 (29) | 23 (10) | 87 (55) |
| | + | (IV) | 71 (71) | 77 (28) | 13 (8) |
| IV, Pea | − | (V) | 8 (6) | 18 (5) | 77 (6) |
| | + | (VI) | 92 (65) | 82 (23) | 3 (2) |
| III, E-PHA | − | (VII) | 68 (20) | 61 (6) | 100 (55) |
| | + | (VIII) | 32 (9) | 39 (4) | − (—) |
| VII, Pea | − | (IX) | 45 (9) | 48 (3) | 68 (37) |
| | + | (X) | 55 (11) | 52 (3) | 32 (18) |
| VII L-PHA | − | (XI) | 23 (5) | 34 (2) | 9 (5) |
| | + | (XII) | 77 (15) | 66 (4) | 91 (50) |

The material which elutes in direct eluate, in phosphate buffered saline (PBS), is designated with a minus sign, and the materials retarded (E-PHA and L-PHA) or specifically displaced by 25 mM α-methylmannoside in PBS (Con A and Pea) are designated with a plus sign. Each fraction is designated with a number to simplify identification of the glycans. For example, fraction XII is material which was not retained during elution on either immobilized Con A or immobilized E-PHA, fraction III and VII, respectively, and was retarded during elution on immobilized L-PHA.

The glycans were first fractionated by chromatography on immobilized PWM and Con A. The total eluate from the immobilized PWM was counted. Only a portion of the eluates from the Con A columns was counted. The materials eluted in PBS (fraction III) and hapten (fraction IV) were separately pooled and subsequently analyzed. Fraction IV was analyzed by chromatography on immobilized pea lectin. Fraction III was analyzed by chromatography on immobilized E-PHA. The materials directly eluted (fraction VII) and retarded (fraction VIII) by this lectin were separately pooled. Fraction VII was then analyzed by chromatography on immobilized pea lectin and the materials eluted in PBS (fraction IX) and hapten (fraction X) were separately pooled. Fraction VII was also analyzed by chromatography on immobilized L-PHA, and the material eluted directly in PBS (fraction XI) and the materials retarded during elution (fraction XII) were separately pooled. Owing to the diminished amount of material available because of these sequential fractionations, elution profiles were obtained by counting a small portion of each fraction, pooling appropriate fractions, and then counting the pooled materials. The table reports the relative amounts in each pooled fraction and in parentheses provides an estimate of the percentage of the original sample in each pooled fraction.

There is an overall similarity between the lectin binding properties of the large native recombinant glycans, and distinct differences between the lectin binding properties of the large and small native glycans. For example, most of the large glycans from both sources are retained by Con A, fraction IV, whereas very few small glycans are retained. In addition, the large glycans are the only glycans to be retained by either pokeweed mitogen, fraction II, or E-PHA, fraction VIII. The size, enzyme sensitivity, and the apparent affinities for QAE-Sephadex and the lectins reported in Table 1 suggest the predominant small native glycans to be triantennary complex-type glycans with either two or three sialic acids.

Fractionation of Recombinant Glycans

The interaction of recombinant glycans with PWM and their sensitivity to endo-$\beta$-galactosidase identifies them as polylactosamine-containing, and the analyses reported in Table 1 provide a general description of their core structures. A more detailed examination of these glycans has been carried out to obtain a better understanding of the organization and decoration of these glycans.

Recombinant glycans were fractionated by gel filtration chromatography on PWM Bio-Gel P4, columns as described above, and the material eluted in PBS (62%) and the material retained were further analyzed by affinity chromatography on immobilized agglutinins from *Triticum vulgaris* (wheat germ, WGA), (Sigma Chemical Co.), *Solanum tuberosum* (potato, STA), (Sigma Chemical Co.), and *Datura stamonium* (jimson weed, DSA) (E-Y Laboratories, Inc.). The glycans not retained by PWM showed almost no interaction with these lectins. The glycans retained by PWM were fractionated into various affinity classes that were sequentially eluted with 10 ml PBS, and then 10 ml aliquots of PBS containing 0.1M GlcNAc, 1.0M GlcNAc and 5 mM N,N'N''-tri-N-acetylchitotriose. These lectins have been demonstrated to interact with various polylactosamine standards and, while their binding determinants have not been precisely defined, the fractionation of the PWM-positive glycans by these lectins indicates heterogeneity in the arrangement of the N-acetyllactosamine repeating units or in their decoration. Wheat germ agglutinin has been demonstrated to interact with sialylated glycans. Therefore, whether the heterogeneous interaction of the glycans with immobilized WGA was a result of heterogeneity in the degree of sialylation was examined. Treatment of the PWM positive material with 0.5 U neuraminidase in 0.1 M citrate, pH 5.5 at 37° C. for 4 hours under a toluene overlay had no effect upon the elution pattern from immobilized WGA. However, examination of the PWM positive material before and after neuraminidase digestion by ion exchange chromatography to test whether the neuraminidase digestion was complete revealed the PWM positive material to be essentially uncharged even prior to neuraminidase digestion. Similar examination of the PWM negative material by ion exchange chromatography revealed a spectrum of glycans with the predominant species having two and three sialic acids. The ion exchange chromatography in these two instances was performed on 0.5 ml columns of QAE-Sephadex (Sigma Chemical Co.). The column was equilibrated with 2 mM Tris·HCl, pH 8.0, and the sample was loaded in this buffer. The column was eluted sequentially with 5-ml aliquots of this buffer containing the following KCl concentrations: 0, 20, 50, 70, 110, 150, 200, and 1,000 mM.

The recombinant glycans have also been examined for their decorations by affinity chromatography over a variety of carbohydrate binding proteins that recognize nonreducing terminal decorations. These proteins fall into the following major groups: Sepharose-immobilized lectins (agglutinins from *Ricinus communis* $RCA_1$ and $RCA_2$), *Dolichos biflorus* (DBA), *Bandieraea simplicifolia* (BSA), soybean (SBA), and peanut (PNA), all available from Sigma Chemical Co.), which interact with terminal Gal and Gal NAc residues linked either $\alpha$ or $\beta$, and Sepharose-immobilized lectins (agglutinins from *Ulex europaeus* (UEA) and *Lotus tetragonolobus* (LTA), both available from Sigma Chemical Co.), and a commercially available monoclonal antibody (SSEA-1), which interact with terminal fucose decorations. None of these immobilized proteins was found to retain any of the recombinant glycans using lectin affinity chromatography where $RCA_1$, $RCA_2$, SBA, DBA, PNA and BSA were eluted with 10 ml PBS and 10 ml PBS containing 0.2M lactose, and UEA, LTA and SSEA-1 were eluted with 10 ml PBS and 10 ml PBS containing 0.2M fucose.

The predominant glycan has a biantennary structure; however, most of the glycans produced by exhaustive digestion with endo-$\beta$-galactosidase are larger than the biantennary complex-type glycan core that would be expected to be the major digestion product. This would elute between fractions 45 and 48. The nature of this endo-$\beta$-galactosidase resistant material has been explored. Examination of the endo-$\beta$-galactosidase digestion products of fetal erythroglycans (currently the best studied polylactosamine material, REFS) has demonstrated that even relatively small glycans are still retained by immobilized PWM. This suggests that the glycan that is recognized by PWM is relatively close to the mannose core. In addition, examination of the smaller native glycans has demonstrated that sialylation can also significantly contribute to the apparent molecular size. The endo-$\beta$-galactosidase digestion products were examined by affinity chromatography on immobilized PWM and by ion exchange chromatography by techniques as described above. The digestion products showed a similar level of interaction with immobilized PWM and showed only a slightly reduced average level of sialylation.

Glycans were fractionated by affinity chromatography on columns of immobilized PWM as described above, and the positive (retained) and negative (eluted directly by PBS) fractions were separately pooled and digested with endo-$\beta$ galactosidase as described above. The digestion products were analyzed by gel filtration on mixed bed columns of Bio-Gel P4/P10. The digestion products from the PWM positive and negative fractions showed similar size distributions. The digestion products of the PWM positive material were then examined by affinity chromatography on immobilized PWM while the digestion products of the PWM negative material were examined by ion exchange chromatography. Although truncated by endo-$\beta$-galactosidase digestion, mannose-labeled glycans that were previously retained by immobilized PWM were still retained after digestion. Mannose-labeled glycans that were not retained by immobilized PWM showed an average loss of one sialic acid on exhaustive endo-$\beta$-galactosidase digestion. The results of these experiments demonstrate that, like fetal erythroglycan, the recombinant glycans carry a determinant that is recognized by PWM close to the mannose core. They also demonstrate that sialic acid contributes to the apparent size of the endo-$\beta$-galactosidase digestion products of the PWM negative material. However, gel filtration of the combined endo-$\beta$-galactosidase and neuraminidase digestion of the PWM negative (non-retained) material showed that it resulted in a smaller apparent size than sequential endo-$\beta$-galactosidase and neuraminidase digestions, suggesting that sialic acid may directly shield potential endo-$\beta$-galactosidase cleavage sites.

In conclusion, on comparing the glycosylation pattern of human IFN-$\beta$ expressed at high levels in CHO cells with that of native human IFN-$\beta$ expressed by induced human fibroblasts, it is clear that interferon molecules from both sources carry asparagine-linked glycans; however, their glycosylation patterns differ in the following respects. The glycans carried by recombinant IFN-$\beta$ molecules from CHO cells are exclusively composed of large, repeating copolymers of galactose and N-acetylglucosamine. More than one third of these glycans are branched and form receptors for pokeweed mitogen. The predominant mannose core is fucosylated and carries two polylactosamine antennae. In contrast, the glycans carried by native interferon molecules are a mixture of large and small glycans. The small glycans have antennae composed of single N-acetyllactosamine units.

The E. coli strains containing plasmids pGC10 and pMI7 were deposited with the American Type Culture Collection, 12301 Parklawn Drive, Rockville, Md. 20852 USA under the conditions of the Budapest Treaty and have the following deposit numbers and dates:

| Strain | CMCC No. | ATCC No. | Deposit Date |
| --- | --- | --- | --- |
| E. coli pGC10 | 1716 | 53251 | 9/11/85 |
| E. coli pM17 | 1723 | 53252 | 9/11/85 |

In summary, the invention herein illustrates that lipophilic protein genes, particularly human IFN genes, may be expressed at high levels in mammalian host cells. For HIFN-$\beta_1$ produced in CHO cells, the specific activity was of the order of $5 \times 10^8$ U/ml: about $3 \times 10^7$ U/ml for IFN-$\beta 1$ produced in E. coli , and about $5 \times 10^8$ U/ml for native human IFN-$\beta_1$. CHO cells offer the major advantage of not coproducing detectable levels of hamster IFN, inductive or constitutive, whether an endogenous or heterologous promoter is used. CHO cells are also observed to be resistant to the anticellular activity of human IFN. Mouse cells, when transformed with IFN gene with its own promoter sequence, produce both human and mouse IFNs, but with a heterologous promoter, no detectable levels of mouse IFN are detected. The IFN-$\beta$ produced in CHO cells was found to have a different composition from that of native human IFN-$\beta$ in that the former contains only large glycans, whereas the latter contains both small and large glycans. Since these IFNs are secreted into the medium and with no contamination by the host IFN, or by endogenous host toxins, the IFN products obtained in accordance with the subject invention would be eminently suitable as therapeutic agents in the treatment of cancer and viral diseases.

The foregoing description of the preferred embodiments of the instant invention have been presented for purposes of illustration and description. It is not intended to be exhaustive or to limit the invention to the precise forms disclosed, and obviously many modifications and variations are possible in the light of the above teaching. The particular embodiments were chosen and described in order to explain best the principles of the invention and its practical application, thereby to enable others skilled in the art to utilize best the invention in various embodiments and with various modifications as are suited to the particular use contemplated. It is intended that the scope of the invention be defined by the claims appended hereto.

What is claimed is:

1. A DNA construct for the expression of the human interferon gene in Chinese hamster ovary cells or progeny thereof comprising an operable linkage of:
    (a) a nucleotide sequence from a cloning vector which allows for replication in a prokaryotic cell;
    (b) a first gene capable of transcription and translation in Chinese hamster ovary cells or progeny thereof operably linked to a selectable marker for the selection of Chinese hamster ovary cell transformants or progeny thereof; and
    (c) a human interferon gene capable of transcription and translation in Chinese hamster ovary cells or progeny thereof.

2. A DNA construct according to claim 1, wherein said DNA construct and said cloning vector are plasmids and said prokaryotic cell is E. coli.

3. A DNA construct according to claim 2, wherein said marker is dihydrofolate reductase or antibiotic resistance.

4. A DNA construct according to claim 3, wherein said marker is dihydrofolate reductase.

5. A DNA construct according to claim 4, wherein said interferon is human IFN-$\alpha$76, IFN-$\alpha$61 , or IFN-$\beta_1$.

6. A DNA construct according to claim 1, wherein said interferon gene and said first genes are operably linked to a promoter for each gene.

7. A DNA construct according to claim 6, wherein said interferon gene is operably linked to a promoter which is endogenous to said interferon gene.

8. A DNA construct according to claim 6, wherein said interferon gene is operably liked to a heterologous promoter.

9. A DNA construct according to claim 6, wherein said first gene is operably linked to SV40 early promoter.

10. A DNA construct according to claim 6, wherein said first gene is operably linked to MMTV promoter.

11. A DNA construct according to claim 8, wherein said heterologous promoter is the SV40 early promoter.

12. A DNA construct according to claim 1, capable of expression in Chinese hamster ovary cells or progeny thereof in culture.

13. A method for the production of human interferon in Chinese hamster ovary cells or progeny thereof comprising:
    (a) introducing into a Chinese hamster ovary cell or progeny thereof a DNA construct comprising an operable linkage of:
        (i) a nucleotide sequence from a cloning vector which allows for replication in a prokaryotic cell;
        (ii) a first gene capable of transcription and translation in Chinese hamster ovary cells or progeny thereof operably linked to a selectable marker for the selection of Chinese hamster ovary cells or progeny thereof; and
        (iii) a human interferon gene capable of transcription and translation in Chinese hamster ovary cells or progeny thereof
        to produce transformants,
    (b) selecting transformed cells,
    (c) growing selected transformants under selective conditions whereby the interferon gene in said DNA construct is expressed, and
    (d) selecting mutants of the grown transformants which are resistant to the negative growth effects of human interferon.

14. A method according to claim 13, wherein said interferon is IFN-β.

15. A method according to claim 14, wherein said interferon is glycosylated.

16. A method according to claim 13, further comprising the steps of isolating and purifying the expressed interferon.

17. A method according to claim 13, wherein said DNA construct is integrated into the chromosome of said host.

18. A method according to claim 13, wherein the selectable marker on the first gene of the DNA construct is dihydrofolate reductase and step (b) is carried out in the presence of methotrexate.

19. A Chinese hamster ovary cell produced according to the method of claim 13.

20. A method according to claim 13 wherein step (c) is carried out under superinduction conditions in the presence of double-stranded RNA and one or more inhibitors of protein synthesis.

21. A method according to claim 20 wherein the double-stranded RNA is poly (1): poly (C) and the inhibitor of protein synthesis is cycloheximide.

* * * * *

UNITED STATES PATENT AND TRADEMARK OFFICE
CERTIFICATE OF CORRECTION

PATENT NO. : 4,966,843
DATED : October 30, 1990
INVENTOR(S) : Francis P. McCormick et al.

It is certified that error appears in the above-indentified patent and that said Letters Patent is hereby corrected as shown below:

Column 1, line 4:

Add - - This invention was made with Goverment support under contract G-M25821 awarded by the National Institute of Health. The Goverment has certain rights in this invention - -.

Signed and Sealed this

Tenth Day of January, 1995

Attest:

BRUCE LEHMAN

Attesting Officer

Commissioner of Patents and Trademarks